United States Patent
Casado et al.

(10) Patent No.: US 11,000,517 B2
(45) Date of Patent: *May 11, 2021

(54) DOSAGE AND FORMULATION

(71) Applicant: Almirall, S.A., Barcelona (ES)

(72) Inventors: Rosa Lamarca Casado, Barcelona (ES); Gonzalo De Miquel Serra, Barcelona (ES)

(73) Assignee: Almirall, S.A., Barcelona (ES)

( * ) Notice: Subject to any disclaimer, the term of this patent is extended or adjusted under 35 U.S.C. 154(b) by 0 days.

This patent is subject to a terminal disclaimer.

(21) Appl. No.: 16/019,855

(22) Filed: Jun. 27, 2018

(65) Prior Publication Data

US 2018/0303806 A1    Oct. 25, 2018

Related U.S. Application Data

(63) Continuation of application No. 13/692,032, filed on Dec. 3, 2012, now Pat. No. 10,085,974, which is a continuation of application No. 12/921,921, filed as application No. PCT/EP2009/001832 on Mar. 13, 2009, now abandoned.

(30) Foreign Application Priority Data

Mar. 13, 2008   (EP) .................................... 08382010

(51) Int. Cl.
| | | |
|---|---|---|
| *A61K 31/439* | (2006.01) | |
| *A61K 9/00* | (2006.01) | |
| *A61K 31/46* | (2006.01) | |
| *A61K 31/167* | (2006.01) | |
| *A61K 45/06* | (2006.01) | |

(52) U.S. Cl.
CPC .......... *A61K 31/439* (2013.01); *A61K 9/0075* (2013.01); *A61K 31/167* (2013.01); *A61K 31/46* (2013.01); *A61K 45/06* (2013.01)

(58) Field of Classification Search
CPC .. A61K 31/439; A61K 9/0075; A61K 31/167; A61K 31/46; A61K 45/06
See application file for complete search history.

(56) References Cited

U.S. PATENT DOCUMENTS

| | | |
|---|---|---|
| 3,091,570 A | 5/1963 | Biel |
| 3,714,357 A | 1/1973 | Gueremy et al. |
| 4,224,332 A | 9/1980 | Gueremy et al. |
| 4,338,931 A | 7/1982 | Cavazza |
| 4,579,854 A | 4/1986 | Iwakuma et al. |
| 4,644,033 A | 2/1987 | Gnanou et al. |
| 4,675,326 A | 6/1987 | Amitai et al. |
| 4,843,074 A | 6/1989 | Rzeszotaraski et al. |
| 4,855,290 A | 8/1989 | Fisher et al. |
| 5,201,308 A | 4/1993 | Newhouse |
| 5,254,330 A | 10/1993 | Ganderton et al. |
| 5,263,475 A | 11/1993 | Altermatt et al. |
| 5,290,539 A | 3/1994 | Marecki |
| 5,290,815 A | 3/1994 | Johnson et al. |
| 5,435,301 A | 7/1995 | Herold et al. |
| 5,507,281 A | 4/1996 | Kuhnel et al. |
| 5,569,447 A | 10/1996 | Lee et al. |
| 5,575,280 A | 11/1996 | Gupte et al. |
| 5,610,163 A | 3/1997 | Banholzer et al. |
| 5,617,845 A | 4/1997 | Poss et al. |
| 5,654,314 A | 8/1997 | Banholzer et al. |
| 5,676,930 A | 10/1997 | Jager et al. |
| 5,685,294 A | 11/1997 | Gupte et al. |
| 5,885,834 A | 3/1999 | Epstein |
| 5,962,505 A | 10/1999 | Bobrove et al. |
| 5,964,416 A | 10/1999 | Jaeger et al. |
| 6,150,415 A | 11/2000 | Hammock et al. |
| 6,299,861 B1 | 10/2001 | Banholzer et al. |
| 6,299,863 B1 | 10/2001 | Aberg et al. |
| 6,402,055 B1 | 6/2002 | Jaeger et al. |
| 6,410,563 B1 | 6/2002 | Deschenes et al. |
| 6,423,298 B2 | 7/2002 | McNamara et al. |
| 6,433,027 B1 | 8/2002 | Bozung et al. |
| 6,455,524 B1 | 9/2002 | Bozung et al. |
| 6,475,467 B1 | 11/2002 | Keller et al. |
| 6,481,435 B2 | 11/2002 | Hochrainer et al. |
| 6,497,373 B2 | 12/2002 | Jaeger et al. |
| 6,521,260 B1 | 2/2003 | Staniforth |
| 6,521,261 B2 | 2/2003 | Sherwood et al. |
| 6,537,524 B1 | 3/2003 | Hassan et al. |
| 6,608,054 B2 | 8/2003 | Meade et al. |
| 6,620,438 B2 | 9/2003 | Pairet et al. |
| 6,680,345 B2 | 1/2004 | Linz et al. |
| 6,686,346 B2 | 2/2004 | Nilsson et al. |
| 6,696,042 B2 | 2/2004 | Pairet et al. |
| 6,706,726 B2 | 3/2004 | Meissner et al. |
| 6,726,124 B2 | 4/2004 | Jaeger et al. |
| 6,749,015 B2 | 6/2004 | Moreau |
| 6,750,226 B2 | 6/2004 | Forner et al. |
| 6,756,508 B2 | 6/2004 | Linz et al. |
| 6,814,953 B2 | 11/2004 | Banerjee et al. |

(Continued)

FOREIGN PATENT DOCUMENTS

| | | |
|---|---|---|
| AU | 2002257587 | 9/2002 |
| AU | 2003236784 B2 | 9/2003 |
| AU | 2003216921 | 10/2003 |
| AU | 2005202144 B2 | 6/2005 |
| CA | 2062854 | 9/1992 |

(Continued)

OTHER PUBLICATIONS

U.S. Appl. No. 10/047,464, filed Jan. 14, 2002, Fernandez Forner et al.
U.S. Appl. No. 10/740,264, filed Dec. 17, 2003, Dolors Fernandez Forner et al.
U.S. Appl. No. 10/891,552, filed Jul. 15, 2004, Meade et al.

(Continued)

*Primary Examiner* — Michael P Cohen
(74) *Attorney, Agent, or Firm* — Finnegan, Henderson, Farabow, Garrett & Dunner, LLP

(57) ABSTRACT

The present disclosure relates to pharmaceutical compositions for inhalation comprising aclidinium in the form of a dry powder of a pharmaceutically acceptable salt in admixture with a pharmaceutically acceptable dry powder carrier, providing a metered nominal dose of aclidinium equivalent to about 400 micrograms aclidinium bromide.

29 Claims, No Drawings

(56) References Cited

U.S. PATENT DOCUMENTS

| | | |
|---|---|---|
| 6,887,459 B1 | 5/2005 | Haeberlin |
| 6,890,517 B2 | 5/2005 | Dreschel et al. |
| 6,918,547 B2 | 7/2005 | Jaeger et al. |
| 6,919,325 B2 | 7/2005 | Linz et al. |
| 6,924,292 B2 | 8/2005 | Kawano et al. |
| 6,986,346 B2 | 1/2006 | Hochrainer et al. |
| 7,040,311 B2 | 5/2006 | Hochrainer et al. |
| 7,078,412 B2 | 7/2006 | Fernandez Forner et al. |
| 7,104,470 B2 | 9/2006 | Jaeger et al. |
| 7,109,210 B2 | 9/2006 | Fernandez Forner et al. |
| 7,122,558 B2 | 10/2006 | Prat Quinones et al. |
| 7,141,671 B2 | 11/2006 | Mammen et al. |
| 7,192,978 B2 | 3/2007 | Quinones et al. |
| 7,196,098 B2 | 3/2007 | Fernandez Forner et al. |
| 7,214,687 B2 | 5/2007 | Fernandez Forner et al. |
| RE39,820 E | 9/2007 | Banholzer et al. |
| 7,358,260 B2 | 4/2008 | Fernandez Forner et al. |
| 7,569,581 B2 | 8/2009 | Meissner et al. |
| 7,750,023 B2 | 7/2010 | Fernandez Forner et al. |
| 7,776,315 B2 | 8/2010 | Pairet et al. |
| 7,897,617 B2 | 3/2011 | Fernandez Forner et al. |
| 8,129,405 B2 | 3/2012 | Fernandez Forner et al. |
| 8,513,279 B2 | 8/2013 | Fernandez Forner et al. |
| 8,802,699 B2 | 8/2014 | Fernandez Forner et al. |
| 9,056,100 B2 | 6/2015 | Fernandez Forner et al. |
| 9,254,262 B2 | 2/2016 | Casado et al. |
| 9,333,195 B2 | 5/2016 | Fernandez Forner et al. |
| RE46,417 E | 5/2017 | Fernandez Forner et al. |
| 9,687,478 B2 | 6/2017 | Fernandez Forner et al. |
| 9,737,520 B2 | 8/2017 | Garcia Gil et al. |
| 2002/0025299 A1 | 2/2002 | Lewis et al. |
| 2002/0052312 A1 | 5/2002 | Reiss et al. |
| 2002/0115680 A1 | 8/2002 | Meissner et al. |
| 2002/0119991 A1 | 8/2002 | Meissner et al. |
| 2002/0122773 A1 | 9/2002 | Pairet et al. |
| 2002/0134538 A1 | 9/2002 | Moreau |
| 2002/0137764 A1 | 9/2002 | Dreschel et al. |
| 2002/0151541 A1 | 10/2002 | Pairet et al. |
| 2002/0151597 A1 | 10/2002 | Banerjee et al. |
| 2002/0179087 A1 | 12/2002 | Bozung et al. |
| 2002/0183292 A1 | 12/2002 | Pairet et al. |
| 2002/0189610 A1 | 12/2002 | Bozung et al. |
| 2002/0193392 A1 | 12/2002 | Schmelzer et al. |
| 2002/0193393 A1 | 12/2002 | Pairet et al. |
| 2003/0018019 A1 | 1/2003 | Meade et al. |
| 2003/0018061 A1 | 1/2003 | Ogawa et al. |
| 2003/0085480 A1 | 5/2003 | Yang |
| 2003/0096834 A1 | 5/2003 | Jenkins et al. |
| 2003/0130300 A1 | 7/2003 | Linz et al. |
| 2003/0139369 A1 | 7/2003 | Yeadon |
| 2003/0158196 A1 | 8/2003 | Jung et al. |
| 2003/0199539 A1 | 10/2003 | Germeyer et al. |
| 2003/0199545 A1 | 10/2003 | Grauert et al. |
| 2003/0203925 A1 | 10/2003 | Meade et al. |
| 2003/0216329 A1 | 11/2003 | Robinson et al. |
| 2004/0002548 A1 | 1/2004 | Bozung et al. |
| 2004/0024007 A1 | 2/2004 | Pairet et al. |
| 2004/0058950 A1 | 3/2004 | Meade et al. |
| 2004/0087617 A1 | 5/2004 | Meissner et al. |
| 2004/0151770 A1 | 8/2004 | Pairet et al. |
| 2004/0161386 A1 | 8/2004 | Pairet et al. |
| 2004/0167167 A1 | 8/2004 | Mammen et al. |
| 2004/0176338 A1 | 9/2004 | Pairet et al. |
| 2004/0184995 A1 | 9/2004 | Katsuma et al. |
| 2004/0192675 A1 | 9/2004 | Pairet et al. |
| 2004/0266869 A1 | 12/2004 | Montague et al. |
| 2005/0025718 A1 | 2/2005 | Meade et al. |
| 2005/0026886 A1 | 2/2005 | Meade et al. |
| 2005/0026887 A1 | 2/2005 | Meade et al. |
| 2005/0026948 A1 | 2/2005 | Meade et al. |
| 2005/0147564 A1 | 7/2005 | Dreschel et al. |
| 2005/0175547 A1 | 8/2005 | Maus et al. |
| 2005/0175548 A1 | 8/2005 | Goede et al. |
| 2005/0175549 A1 | 8/2005 | Goede et al. |
| 2005/0209272 A1 | 9/2005 | Fernandez Forner et al. |
| 2005/0244339 A1 | 11/2005 | Jauernig et al. |
| 2005/0256149 A1 | 11/2005 | Linz et al. |
| 2005/0267078 A1 | 12/2005 | Gras Escardo et al. |
| 2005/0267135 A1 | 12/2005 | Escardo et al. |
| 2005/0282875 A1 | 12/2005 | Prat Quinones |
| 2005/0288266 A1 | 12/2005 | Gras Escardo et al. |
| 2006/0030579 A1 | 2/2006 | Park et al. |
| 2006/0057074 A1 | 3/2006 | Meade et al. |
| 2006/0079540 A1 | 4/2006 | Schmidt |
| 2006/0106055 A1 | 5/2006 | Fernandez Forner et al. |
| 2006/0106056 A1 | 5/2006 | Fernandez Forner et al. |
| 2006/0154934 A1 | 7/2006 | Escardo et al. |
| 2006/0189651 A1 | 8/2006 | Gras Escardo et al. |
| 2006/0196500 A1 | 9/2006 | Hochrainer et al. |
| 2006/0205702 A1 | 9/2006 | Escardo et al. |
| 2006/0252790 A1 | 11/2006 | Allen et al. |
| 2006/0285987 A1 | 12/2006 | Jaeger et al. |
| 2007/0128125 A1 | 6/2007 | Schmelzer et al. |
| 2008/0214600 A1 | 9/2008 | Fernandez Forner et al. |
| 2009/0088408 A1 | 4/2009 | Meade et al. |
| 2009/0299042 A1 | 12/2009 | Busquets Baque et al. |
| 2010/0234333 A1 | 9/2010 | Fernandez Forner et al. |
| 2010/0310477 A1 | 12/2010 | Pairet et al. |
| 2010/0330186 A1 | 12/2010 | Meade et al. |
| 2011/0020412 A1 | 1/2011 | Lamarca Casado et al. |
| 2011/0020454 A1 | 1/2011 | Lamarca Casado et al. |
| 2011/0021477 A1 | 1/2011 | Gras Escardo et al. |
| 2011/0021478 A1 | 1/2011 | Gras Escardo et al. |
| 2011/0038806 A1 | 2/2011 | Meade et al. |
| 2011/0118223 A1 | 5/2011 | Fernandez Forner et al. |
| 2011/0243924 A1 | 10/2011 | Beleta Supervia |
| 2012/0040943 A1 | 2/2012 | Gras Escardo et al. |
| 2012/0302532 A1 | 11/2012 | Gras Escardo et al. |
| 2012/0309727 A1 | 12/2012 | Gras Escardo et al. |
| 2013/0035319 A1 | 2/2013 | Gras Escardo et al. |
| 2013/0125884 A1 | 5/2013 | Lamarca Casado et al. |
| 2013/0189317 A1 | 7/2013 | Lamarca Casado et al. |
| 2013/0196961 A1 | 8/2013 | Gras Escardo et al. |
| 2013/0252928 A1 | 9/2013 | Gras Escardo et al. |
| 2013/0310354 A1 | 11/2013 | Gras Escardo et al. |
| 2014/0094442 A1 | 4/2014 | Gras Escardo et al. |
| 2014/0100246 A1 | 4/2014 | Garcia Gil et al. |
| 2014/0296197 A1 | 10/2014 | Gras Escardo et al. |
| 2015/0080359 A1 | 3/2015 | Gras Escardo et al. |
| 2015/0093374 A1 | 4/2015 | Beleta Supervia |
| 2015/0118312 A1 | 4/2015 | Lamaraca Casado et al. |
| 2015/0246026 A1 | 9/2015 | Fernandez Forner et al. |
| 2015/0328194 A1 | 11/2015 | Jarreta Fernandez et al. |
| 2016/0263091 A1 | 9/2016 | Garcia Gil et al. |
| 2016/0296503 A1 | 10/2016 | Fernandez Forner et al. |
| 2016/0331733 A1 | 11/2016 | Jarreta Fernandez et al. |
| 2017/0049756 A1 | 2/2017 | Gras Escardo et al. |
| 2017/0128426 A1 | 5/2017 | Lamarca Casado et al. |

FOREIGN PATENT DOCUMENTS

| | | |
|---|---|---|
| CA | 2429012 | 5/2002 |
| CA | 2436540 A1 | 5/2002 |
| CA | 2455167 | 1/2003 |
| CA | 2459493 | 3/2003 |
| CA | 2516467 | 9/2004 |
| DE | 10216333 | 10/2003 |
| EP | 0003445 | 8/1979 |
| EP | 0069715 | 1/1983 |
| EP | 0166294 | 1/1986 |
| EP | 0302699 | 2/1989 |
| EP | 0 418 716 A1 | 3/1991 |
| EP | 0424021 A1 | 4/1991 |
| EP | 0424790 A1 | 5/1991 |
| EP | 0505321 | 9/1992 |
| EP | 0205247 B1 | 12/1992 |
| EP | 0424790 B1 | 8/1993 |
| EP | 0 424 021 B1 | 3/1994 |
| EP | 0418716 B1 | 4/1994 |
| EP | 0 747 355 | 12/1996 |
| EP | 0801067 A1 | 10/1997 |
| EP | 0603229 B1 | 6/1998 |
| EP | 0 801 067 B1 | 3/2003 |
| EP | 1 087 750 B1 | 11/2003 |

(56) References Cited

FOREIGN PATENT DOCUMENTS

| | | |
|---|---|---|
| EP | 1452179 | 9/2004 |
| EP | 1471919 B1 | 8/2005 |
| EP | 1651270 B1 | 3/2007 |
| EP | 1 763 369 B1 | 12/2008 |
| EP | 1763368 B1 | 3/2009 |
| EP | 2100599 | 9/2009 |
| ES | 2 165 768 | 3/2002 |
| ES | 2 206 021 | 5/2004 |
| ES | 2 239 546 | 9/2005 |
| FR | 2012964 | 3/1970 |
| GB | 1219606 | 1/1971 |
| GB | 2041763 | 9/1980 |
| GB | 2165159 | 4/1986 |
| GB | 2242134 | 9/1991 |
| GB | 2419819 | 5/2006 |
| HU | 178679 | 6/1982 |
| MX | PA03008045 | 12/2003 |
| WO | WO 1987/007502 | 12/1987 |
| WO | WO 1991/002558 | 3/1991 |
| WO | WO 1991/004252 | 4/1991 |
| WO | WO 1991/014468 | 10/1991 |
| WO | WO 1992/000771 | 1/1992 |
| WO | WO 1992/004928 | 2/1992 |
| WO | WO 1992/003175 | 3/1992 |
| WO | WO 1992/004068 | 3/1992 |
| WO | WO 1992/004345 | 3/1992 |
| WO | WO 1992/004346 | 3/1992 |
| WO | WO 1992/009322 | 6/1992 |
| WO | WO 1994/014492 | 7/1994 |
| WO | WO 1995/024889 | 9/1995 |
| WO | WO 1996/004346 | 2/1996 |
| WO | WO 1996/019968 | 7/1996 |
| WO | WO 1996/032150 | 10/1996 |
| WO | WO 1997/000703 | 1/1997 |
| WO | WO 1997/001337 | 1/1997 |
| WO | WO 1997/012687 | 4/1997 |
| WO | WO 1997/028801 | 8/1997 |
| WO | WO 1997/034871 | 9/1997 |
| WO | WO 1998/015280 | 4/1998 |
| WO | WO 1999/051205 | 10/1999 |
| WO | WO 1999/065464 | 12/1999 |
| WO | WO 2000/005219 | 2/2000 |
| WO | WO 2000/047200 | 8/2000 |
| WO | WO 2001/004118 | 1/2001 |
| WO | WO 2001/012167 | 2/2001 |
| WO | WO 2001/050080 A2 | 7/2001 |
| WO | WO 2001/050080 A3 | 7/2001 |
| WO | WO 2001/057025 | 8/2001 |
| WO | WO 2001/076601 A2 | 10/2001 |
| WO | WO 2001/076601 A3 | 10/2001 |
| WO | WO 2001/078736 | 10/2001 |
| WO | WO 2001/078739 | 10/2001 |
| WO | WO 2001/078741 | 10/2001 |
| WO | WO 2001/078743 | 10/2001 |
| WO | WO 2001/089491 | 11/2001 |
| WO | WO 2002/009689 | 2/2002 |
| WO | WO 2002/036106 | 5/2002 |
| WO | WO 2002/038154 | 5/2002 |
| WO | WO 2002/047667 | 6/2002 |
| WO | WO 2002/051841 | 7/2002 |
| WO | WO 2002/053564 A2 | 7/2002 |
| WO | WO 2002/053564 A3 | 7/2002 |
| WO | WO 2002/060532 | 8/2002 |
| WO | WO 2002/060533 A2 | 8/2002 |
| WO | WO 2002/060533 A3 | 8/2002 |
| WO | WO 2002/066422 | 8/2002 |
| WO | WO 2002/096423 A2 | 12/2002 |
| WO | WO 2002/096423 A3 | 12/2002 |
| WO | WO 2002/096463 | 12/2002 |
| WO | WO 2003/000241 | 1/2003 |
| WO | WO 2003/000289 | 1/2003 |
| WO | WO 2003/000325 | 1/2003 |
| WO | WO 2003/011274 A2 | 2/2003 |
| WO | WO 2003/011274 A3 | 2/2003 |
| WO | WO 2003/024452 | 3/2003 |
| WO | WO 2003/042160 | 5/2003 |
| WO | WO 2003/061742 | 7/2003 |
| WO | WO 2003/066063 | 8/2003 |
| WO | WO 2003/066063 A1 | 9/2003 |
| WO | WO 2003/074025 A2 | 9/2003 |
| WO | WO 2003/074025 A3 | 9/2003 |
| WO | WO 2003/087094 A2 | 10/2003 |
| WO | WO 2003/087094 A3 | 10/2003 |
| WO | WO 2003/097098 | 11/2003 |
| WO | WO 2003/097613 | 11/2003 |
| WO | WO 2004/005285 | 1/2004 |
| WO | WO 2004/043966 | 5/2004 |
| WO | WO 2004/058729 | 7/2004 |
| WO | WO 2004/074267 | 9/2004 |
| WO | WO 2004/074276 | 9/2004 |
| WO | WO 2004/074276 A1 | 9/2004 |
| WO | WO 2004/084896 | 10/2004 |
| WO | WO 2004/084897 | 10/2004 |
| WO | WO 2005/013993 | 2/2005 |
| WO | WO 2005/013994 | 2/2005 |
| WO | WO 2005/014005 | 2/2005 |
| WO | WO 2005/014044 A1 | 2/2005 |
| WO | WO 2005/049581 | 6/2005 |
| WO | WO 2005/090342 | 9/2005 |
| WO | WO 2005/097126 | 10/2005 |
| WO | WO 2005/115462 | 12/2005 |
| WO | WO 2005/115463 | 12/2005 |
| WO | WO 2005/115464 | 12/2005 |
| WO | WO 2005/115465 A1 | 12/2005 |
| WO | WO 2005/115466 | 12/2005 |
| WO | WO 2005/115467 | 12/2005 |
| WO | WO 2006/105401 | 10/2006 |
| WO | WO 2008/009397 | 1/2008 |
| WO | WO 2008/096121 | 8/2008 |
| WO | WO 2008/102128 | 8/2008 |
| WO | WO 2009/112273 A2 | 9/2009 |
| WO | WO 2009/112273 A3 | 9/2009 |
| WO | WO 2009/112274 A2 | 9/2009 |
| WO | WO 2009/112274 A3 | 9/2009 |
| WO | WO-2009112274 A2 * | 9/2009 ........... A61K 9/0075 |
| WO | WO 2013/175013 A1 | 11/2013 |
| WO | WO 2014/096553 | 6/2014 |

OTHER PUBLICATIONS

U.S. Appl. No. 10/892,033, filed Jul. 15, 2004, Meade et al.
U.S. Appl. No. 11/116,777, filed Apr. 28, 2005, Dolors Fernandez Forner et al.
U.S. Appl. No. 11/141,169, filed May 31, 2005, Gras Escardo.
U.S. Appl. No. 11/141,427, filed May 31, 2005, Gras Escardo.
U.S. Appl. No. 11/141,428, filed May 31, 2005, Gras Escardo.
U.S. Appl. No. 11/324,919, filed Jan. 3, 2006, Fernandez Forner et al.
U.S. Appl. No. 11/325,059, filed Jan. 3, 2006, Fernandez Forner et al.
U.S. Appl. No. 11/636,181, filed Dec. 8, 2006, Fernandez Forner et al.
U.S. Appl. No. 12/074,929, filed Mar. 7, 2008, Fernandez Forner et al.
U.S. Appl. No. 12/374,185, filed Feb. 11, 2009, Basquet's Baque et al.
U.S. Appl. No. 12/528,267, filed Aug. 21, 2009, Beleta Supervia.
U.S. Appl. No. 12/787,772, filed May 26, 2010, Fernandez Forner et al.
U.S. Appl. No. 12/875,601, filed Sep. 3, 2010, Meade et al.
U.S. Appl. No. 12/912,145, filed Oct. 26, 2010, Meade et al.
U.S. Appl. No. 12/921,892, filed Sep. 10, 2010, Lamarca Casado et al.
U.S. Appl. No. 12/921,921, filed Oct. 5, 2010, Lamarca Casado et al.
U.S. Appl. No. 13/011,131, filed Jan. 21, 2011, Fernandez Forner et al.
U.S. Appl. No. 13/672,893, filed Nov. 9, 2012, Rosa Lamarca Casado.
U.S. Appl. No. 13/692,032, filed Dec. 3, 2012, Lamarca Casado et al.

(56) References Cited

OTHER PUBLICATIONS

U.S. Appl. No. 13/862,370, filed Apr. 13, 2013, Gras Escardo et al.
U.S. Appl. No. 14/111,211, filed Oct. 11, 2013, Garcia Gil et al.
U.S. Appl. No. 14/403,220, filed Nov. 24, 2014, Lamarca Casado et al.
U.S. Appl. No. 14/471,819, filed Aug. 14, 2014, Gras Escardo et al.
U.S. Appl. No. 14/549,347, filed Nov. 20, 2014, Gras Escardo et al.
U.S. Appl. No. 14/561,857, filed Dec. 5, 2014, Beleta Supervia.
U.S. Appl. No. 14/652,817, filed Jun. 17, 2015, Diana Jarreta Fernandez et al.
U.S. Appl. No. 14/712,866, filed May 14, 2015, Fernandez Forner et al.
U.S. Appl. No. 14/795,194, filed Jul. 9, 2015, Gras Escardo et al.
U.S. Appl. No. 14/920,519, filed Oct. 22, 2015, Gras Escardo et al.
U.S. Appl. No. 15/019,009, filed Feb. 9, 2016, Fernandez Forner et al.
U.S. Appl. No. 15/080,475, filed Mar. 24, 2016, Gras Escardo et al.
U.S. Appl. No. 15/095,036, filed Apr. 9, 2016, Fernandez Forner et al.
U.S. Appl. No. 15/159,643, filed May 19, 2016, Gras Escardo et al.
U.S. Appl. No. 15/161,531, filed May 23, 2016, Garcia Gil et al.
U.S. Appl. No. 15/218,391, filed Jul. 25, 2016, Jarreta Fernandez et al.
U.S. Appl. No. 15/409,741, filed Jan. 19, 2017, Lamarca Casado et al.
U.S. Appl. No. 15/436,178, filed Feb. 17, 2017, Jarreta Fernandez et al.
U.S. Appl. No. 15/599,646, filed May 19, 2017, Fernandez Forner et al.
U.S. Appl. No. 15/688,679, filed Aug. 28, 2017, Gras Escardo et al.
6001 chemical abstracts, Columbus, OH, US, vol. 104(19). XP-002128290, p. 659 (1985).
ABPI Medicines Compendium 2003: Data Sheets for Atrovent Aerocaps, Atrovent Autohaler, Atrovent Forte MA, Atrovent Metered Dose Inhaler, Atrovent UDVs, pp. 151-155, ISBN 0 907102 20 4.
ABPI Medicines Compendium 2003: Data Sheets for Combivent Metered Aerosol, Combivent UDVs, pp. 439-441, ISBN 0 907102 20 4.
ABPI Medicines Compendium 2003: Data Sheets for Duovent Autohaler, Duovent Inhaler, Duovent UDVs, pp. 643-646, ISBN 0 907102 20 4.
ABPI Medicines Compendium 2003: Data Sheets for Oxivent Autohaler, Oxivalent Inhaler, pp. 1615-1616, SBN 0 907102 20 4.
ABPI Medicines Compendium 2003: Data Sheets for Spiriva, pp. 1999-2001, ISBN 0 907102 20 4.
Alabaster, V., "Discovery and Development or Selective M3 Antagonists for Clinical Use," Life Sciences, 1997, 60 (13/14), 1053-1060.
Alabaster, V., "Discovery and Development or Selective M3 Antagonists for Clinical Use," Life Sciences, vol. 60, 13/14, 1997, 1 page—Abstract Only.
Amakye, D., et al., "Pharmacokinetics (PK) and Pharmacodynamics (PD) of SCI0-469, A P38 Gamma Map Kinase Inhibitor," Clinical Pharmacology and Therapeutics, 2004, 5 (2), P54: Abst PII-7.
Andersson, P, Presentation labeled "Aclidinium bromide, a novel inhaled long-acting anticholinergic", presented Sep. 17, 2007, 16 pages.
Appeal Brief in U.S. Appl. No. 10/892,033 dated Aug. 30, 2010.
Applicant-initiated Interview Summary dated Jan. 27, 2017, in U.S. Appl. No. 13/692,032.
Atkins, P J. et al., "Dry Powder Inhalers: An Overview", Respiratory Care, vol. 50, No. 10, Oct. 2005, pp. 1304-1312.
Atrovent® (ipratropium bromide) Inhalation Solution Prescribing Information, Boehringer Ingelheim International GmbH 830885-R, Revised Oct. 1998.
Atrovent® Aerosol Prescribing Information, Boehringer Ingelheim International GmbH 10001403US/1, 10001403/01, Revised Mar. 27, 2002.
Atrovent® HFA Approved Labeling, Application No. 21-527, Boehringer Ingelheim International GmbH, 2004.
Auerbach, D. et al., "Routine Nebulized Ipratropium and Albuterol Together are Better Than Either Alone in COPD," The COMBIVENT Inhalation Solution Study Group, Chest, 1997 112, 1514-1521.
Avdeyev, S. M., "Anticholinergic Preparations in Obstructive Pulmonary Diseases," Atmosphera, 2002, No. I, pp. 20-23 (English translation attached).
Ayres, JG et al. Thorax 52(Supp 1): S1-S21 (1997).
Bach, P. et al., "Management of Acute Exacerbations of Chronic Obstructive Pulmonary Disease: A Summary and Appraisal of Published Evidence," Annals of Internal Medicine, 2001, 134 (7), 600-620.
Baeumer, et al., "Cilomilast, an orally active phosphodiesterase 4 inhibitor for the treatment of COPD," Expert Rev. Clin. Immunol., 1(1): 27-36 (2005).
Banner, K. et al., "The Effect of Selective Phosphodiesterase 3 and 4 Isoenzyme Inhibitors and Established Anti-Asthma Drugs on Inflammatory Cell Activation," British Journal of Pharmacology, 1996, 119, 1255-1261.
Barnes, P., "Advances in Chronic Obstructive Pulmonary Disease," Ordinary Meeting, Jan. 13, 2003, pp. 41-51.
Barnes, P., "Chronic Obstructive Pulmonary Disease 12: New Treatments for COPD," Thorax, 2003, 58(9), 803-808.
Barnes, P., "COPD: Is There Light at the End of the Tunnel?" Current Opinion in Pharmacology, 2004, 4, 263-272.
Barnes, P., "Future Advances in COPD Therapy," Respiration, 2001, 68, 441-448.
Barnes, P., "New Drugs for Asthma," Nature Reviews, Drug Discovery, 2004, 3, 831-844.
Barnes, P., "The Role of Anticholinergics in Chronic Obstructive Pulmonary Disease," American Journal of Medicine, 2004, 117 (12A), 24S-32S.
Barnes, P. et al., Eds., Asthma and COPD, Basic Mechanisms and Clinical Management, Academic Press, Amsterdam, 2002, ISBN 0-12-079028-9, pp. 523, 530-531, 731.
Barnes, P. et al., Eds., Asthma, vol. 2, Lippincott-Raven, Philadelphia, 1997, ISBN 0-397-51682-7, Chapter 142: Compliance by H. Mawhinney et al., pp. 2099-2113.
Barnes P., Ed., Managing Chronic Pulmonary Disease, Second Edition, Science Press Ltd, London, 2001, ISBN 1-85873-932-2, Chapter 2: Clinical Features, pp. 28-31, 35; Chapter 3: Drugs Used in the Management of COPD, pp. 40-43; Chapter 4: Management of COPD, pp. 57-62, 66; Chapter 5: Future Trends in Therapy, pp. 73-75.
Barnes, P. et al., "COPD: Current Therapeutic Interventions and Future Approaches," European Respiratory Journal, 2005, 25 (6), 1084-1106.
Barnes, P. et al., "Prospects for New Drugs for Chronic Obstructive Pulmonary Disease," Lancet 2004, 364,985-996.
Barnes, P. et al., "The Effect of Platelet Activating Factor on Pulmonary—Adrenoceptors," British Journal of Pharmacology, 1987, 90, 709-715.
Beasley, R. et al., "Withdrawal of Fenoterol and the End of the New Zealand Asthma Mortality Epidemic," International Archives of Allergy and Immunology, 1995, 107, 325-327.
Beeh, K., et al., "Aclidinium Bromide Improves Exercise Endurance and Dynamic Hyperinflamation and Decreases Exertional Dyspnoea In Patients with Moderate-To-Severe COPD," Am J Respir Crit Care Med, 2013; 187: A2430.
Beleta, J., "Discovery of aclidinium bromide; a new long-acting muscarinic antagonist for COPD," Oral Presentation; Society for Medicines Research Symposium, Sep. 11, 2007 (28 pages).
Berenbaum, M., "Synergy, Additivism and Antagonism in Immunosuppression, A Critical Review," Clinical and Experimental Immunology, 1977, 28, 1-18.
Berenbaum, M., "What is Synergy?" Pharmacological Reviews, 1989, 41, 93-141 and Errata, p. 422.
Berkow, R. et al., Eds., The Merck Manual of Diagnosis and Therapy, Sixteenth Edition, 1992, Foreword and Chapter 34, "Airways Obstruction Asthma," pp. 646-657.
Boehringer Ingelheim International GmbH, European Patent No. 1 651 270 B1 as proposed to be amended, 20 pages, first submitted to the U.S. Patent and Trademark Office in U.S. Appl. No. 12/070,298 dated Oct. 19, 2009.

(56) References Cited

OTHER PUBLICATIONS

Bone, R. et al., "In Chronic Obstructive Pulmonary Disease, A Combination of Ipratropium and Albuterol is More Effective that Either Agent Alone: An 85-Day Multicenter Trial," COMBIVENT Inhalation Aerosol Study Group, Chest, 1994, 105, 1411-1419.
Boswell-Smith et al., "Are phosphodiesterase 4 inhibitors just more theophylline?" J. Allergy Clin. Immunology, 117(6): 1237-1243 (Jun. 2006).
Boulet, L P et al., "Canadian asthma consensus report, 1999" CMAJ/JAMC, vol. 161 (11 Suppl), 1999, pp. s1, s44-50.
Braunwald, E. et al., Eds., Harrison's 15th Edition, Principles of Internal Medicine, vol. 2, McGraw-Hill, New York, 2001, ISBN 0-07-007272-4, Section Titled: Chronic Bronchitis, Emphysema, and Airways Obstruction by E.G. Honig et al., pp. 1491, 1495-1496.
British National Formulary 45, Mar. 2003, ISBN 0 7279 1772 2, Chapter 3: Respiratory System, pp. 131-165.
British Thoracic Society, "BTS Guidelines for the Management of Chronic Obstructive Pulmonary Disease," The COPD Guidelines Group of the Standards of Care Committee of the BTS, Thorax, 1997, 52, Supplement 5, SI-S28.
British Thoracic Society, "BTS Guidelines for the Management of Chronic Obstructive Pulmonary Disease," The COPD Guidelines Group of the Standards of Care Committee of the BTS, Thorax, 1997, 52, Supplement 5, S1-S28, retrieved Mar. 13, 2014, from thorax.bmj.com.
British Thoracic Society, British Guideline on the Management of Asthma, Thorax, 2003, 58, Supplement I, il-i94.
Brittain, H G., "What is the "correct" method to use for particle-size determination?" Pharmaceutical Technology, Jul. 2001, pp. 96, 98.
Brodde, "Beta1- and Beta2-Adrenoceptors in the Human Heart: Properties, Function, and Alterations in Chronic Heart Failure," Pharmacological Reviews, 1991, 43 (2), 203-242.
Bryant, D., "Nebulized Ipratropium Bromide in the Treatment of Acute Asthma," Chest, Jul. 1985, pp. 24-29.
Buhl, R. et al., "Future Directions in the Pharmacologic Therapy of Chronic Obstructive Pulmonary Disease," Proceedings of the American Thoracic Society, 2005, 2 (1), 83-93.
Burtner, R. et al., Antispasmodics II, Basic Esters of Some Polynuclear Carboxylic Acids, J. Am. Chem. Soc. 65: 1582-1585 (1943).
Calverley, P.M.A., Ed., Chronic Obstructive Pulmonary Disease, Chapman and Hall, London, 1995, ISBN 0 412 46450, Chapter 16: Bronchodilators: Basic Pharmacology by P.J. Barnes, pp. 391 and 398-401.
Calverley, P.M.A. et al., "Salmeterol and Fluticason Propionate and Survival in Chronic Obstructive Pulmonary Disease," New England Journal of Medicine, 2007,356 (8), 775-789.
Cazzola, M. et al., "The Functional Impact of Adding Salmeterol and Tiotropium in Patients with Stable COPD," Respiratory Medicine, 2004, 98, 1214-1221.
Cazzola, M. et al., "The Pharmacodynamic Effects of Single Inhaled Doses of Formoterol, Tiotropium and Their Combination in Patients with COPD," Pulmonary Pharmacology & Therapeutics, 2004, 17, 35-39.
Chanez, P. et al., "Once-Daily Administration of Aclidinium Bromide, A Novel, Long-Acting Anticholinergic: A Phase II, Dose Finding Study," Eur. Respir. J., vol. 32, 2008, p. 476s, Abstract 2736.
Chanez, P. et al., "Once-Daily Administration of Aclidinium Bromide, A Novel, Long-Acting Anticholinergic: A Phase II, Dose Finding Study," Published as Poster Presentation at European Respiratory Society Annual Congress in Berlin, Germany, 2008, 2 pages.
Christensen et al., "1,4-Cyclohexanecarboxylates: Potent and Selective Inhibitors of Phosphodiesterase 4 for the Treatment of Asthma," J. Med. Chem. 41:821-835 (1998).
Chrystn, H. et al., "The Genuair® inhaler: a novel, multidose dry power inhaler," International Journal of Clinical Practice, vol. 66, No. 3, pp. 309-317 (2012).
Chuchalin A.G. et al: "Clinical Equivalence Trial on Budesonide Delivered either by the Novolizer Multidose Dry Power Inhaler or the Turbuhaler in Asthmatic Patients" Respiration; 69: 502-508 (2002).
Chung, K., "Phosphodiesterase Inhibitors in Airways Disease," European Journal of Pharmacology, 2006, 533, 110-117.
Clarkson, E. et al., "Binding and Active Transport of Large Analogues of Acetylcholine by Cholinergic Synaptic Vesicles In Vitro," Journal of Neurochemistry, 1992, 59, 695-700.
Cohen, VI et al., "Synthesis and Receptor Affinities for New-3-Quinuclidinyl a-Heteroaryl-a-aryl-a-Hydroxyacetates," J. Pharm. Sciences, 81: 326-329 (1992).
COMBIVENT Advertisement in American Journal of Respiratory and Critical Care Medicine, Feb. 1, 2003, 167 (3), 4 pages.
COMBIVENT Advertisement in ATS 2003 Seattle 99th International Conference Final Program, May 16-21, 2003, 4 pages.
COMBIVENT® Advertisement in Chest, 2003, 123 (6), 4 pages.
COMBIVENT, Inhalation Aerosol Prescribing Information, Boehringer Ingelheim International GmbH, 10000291/03, revised Sep. 2001.
Costain, D. et al., "Guidelines for Management of Asthma in Adults: I-Chronic Persistent Asthma," Br. Med. J. 301: 651-653 (1990).
D'Urzo, A. D. et al., "Efficacy and safety of fixed-dose combinations of aclidinium bromide/formoterol fumarate: the 24-week, randomized, placebo-controlled AUGMENT COPD study," Respiratory Research 2014, 15:123, 18 pages.
Davis, MA et al., "New Psychotropic Agents VI, Basic Esters of 5-Hydroxydibenzo[a,d]cycloheptadiene-5-carboxylic acid," J. Med. Chem 6: 513-51 (1963).
Davis, MA et al., "Anticonvulsants I. Dibenzo[a,d]cycloheptadiene-5-carboxamide and Related Compounds," J. Med. Chem 7: 88-94 (1964).
Dent, et al., "Effectis of a Selective PDE4 Inhibitor, D-22888, on Human Airways and Eosinophils In vitro and Late Phase Allergic Pulmonary Eosinophilia in Guinea Pigs," Pulmonary Pharma & Thera. 11:13-21 (1998).
Disse, B., "Antimuscarinic Treatment for Lung Disease, From Research to Clinical Practice," Life Sciences, 2001, 68, 2557-2564.
Disse, B. et al., "BA 679 BR, A Novel Long-Acting Anticholinergic Bronchodilator," Life Sciences, 1993, 52, 537-544.
Dompeling, E. et al., "Slowing the Deterioration of Asthma and Chronic Obstructive Pulmonary Disease Observed During Bronchodilator Therapy by Adding Inhaled Corticosteroids," Annals of Internal Medicine, 1993, 118, 770-778.
Donohue, "Minimal clinically important differences in COPD lung function," Journal of Chronic Obstructive Pulmonary Disease, vol. 2, No. 1, pp. 111-124 (2005) (Abstract).
Down, et al., "Clinical Pharmacology of Cilimast," Clin. Pharmacokinet, 45(3): 217-233 (2006) abstract.
Drug Information Display, "Generic Name: Atropine—Oral, Brand Name(s): Sal-Tropine," obtained from www.medicinenet.com, p. 1 of 3, as of Nov. 4, 2008.
Durham, M. "Tiotropium (Spiriva): a once-daily inhaled anticholinergic medication for chronic obstructive pulmonary disease," BUMC Proceedings, 17: 366-373 (2004).
Dyke, H. et al., "Update on the Therapeutic Potential of PDE4 Inhibitors," Expert Opinion on Investigational Drugs, 2002, 11 (1), 1-13.
Easton, P. et al., "A Comparison of the Bronchodilating Effects of a Beta-2 Andrenergic Agent (Albuterol) and an Anticholinergic Agent (Ipratropium Bromide), Given by Aerosol Alone or in a Sequence," NewEnglandJournalofMedicine, 1986,315 (12), 735-739.
Eglen, R. et al, "Muscarinic Receptor Subtypes and Smooth Muscle Function," Pharmacological Reviews, 1996,48 (4), 531-565.
Eglen, R. et al, "Muscarinic Receptor Subtypes: Pharmacology and Therapeutic Potential," DN & P. 10(8): 462-469 (Oct. 1997).
Emea, "Note for Guidance on Dose Response Information to Support Drug Registration," ICH Topic E 4. 1994. CPMP/ICH/378/95.
English language abstract for DE 10216333, retrieved from the European Patent Office website on Mar. 28, 2013, 2 pages.
English Abstract for Romain, O. et al., "Actualites Pharmaceutiques," (2006) 1596-1598, 13(12), XP027997707, ISSN: 0929-693X, DOI:10.

(56) References Cited

OTHER PUBLICATIONS

1016/J.ARCPED.2006.09.019, Archives De Pediatrie, Elsevier, Paris, FR.
English-language abstract for HU 178679, retrieved from the European Patent Office website on Nov. 21, 2003, 1 page.
English-language abstract for WO 2003/024452.
English language abstract for WO 2003/061742.
English language abstract for WO 2004/074267.
English-language translation of Official Action dated Mar. 25, 2009, in Russian Patent Application No. 2006147250, 3 pages.
English-language Machine Translation of GROB, Ca et al. "Die Synthese von 4-Brom- und 4-Hydrox0Chinuclidin," Helv. Chim. Acta 41: 1184-1191 (1958).
English-language Machine Translation of Konzett, H. et al. "Versuchsanordnung zu Untersuchungnen an der Bronchialmuskulatur," Arch. Exp. Path. Pharmacol. 195: 71-74 (1940).
English-language Machine Translation of Rigaudy, J et al. "Cetones Derivees du Dibzeno [a,d]cycloheptadiene. La Dibenzo-2,3-6,7 Cycloheptadienedione-4,5" Bull. Soc. Chim. France, 638-643 (1959).
English-language translation of p. 1554 of Medical Dictionary, Edited by Ishiyaku Shuppan KK, 2001, 1 page.
English-language translation of p. 96, Table 3-7 of Introduction to Pharmacology, 2003, 1 page.
English-language translation of pp. 20, 23 of Pharmacology Manual, Edited by KK Nanzando,2002, 2 pages.
EP2265258 Office Action dated Apr. 24, 2013, Application No. 09 720 773.2-1445.
EPO Application No. 04763322.7-2123, Third Party Observations dated Jul. 8, 2008.
Etzler, F M. et al., "Particle size analysis; a comparative study of various methods", Part. Part. Syst. Charact., vol. 12, Oct. 1995; pp. 217-224.
European Medicines Agency Assessment Report—Brimica Genuair, Sep. 25, 2014, pp. 1-136.
European Medicines Agency Committee for Medicinal Products for Human Use (CHMP), Guideline on the Pharmaceutical Quality of Inhalation and Nasal Products (2008).
European No. 1 763 369, Notice of Opposition dated Sep. 15, 2009, and English-language translation (27 pages total, 16 pages translation).
European Patent Application No. 05750538.0-2107 Reply to Communication, dated Mar. 11, 2008, 3 pages.
European Patent Application No. 09729773.2 Communication pursuant to Article 94(3) EPC dated Apr. 24, 2013, 9 pages.
European Patent Application No. EP 1 763 369, Notice of Opposition dated Sep. 15, 2009, with English translation (27 pages total, 16 pages translation).
European Patent Application No. 13725154.2 Response dated Jul. 31, 2015, 16 pages.
European Patent Application No. 13725154.2 Response dated Aug. 9, 2016, 3 pages.
European Patent No. 1651270, Decision Revoking the European Patent, dated May 18, 2010, 12 pages.
European Patent No. 1651270, Grounds of Opposition by Laboratorios Almirall S.A., dated Dec. 21, 2007, 12 pages.
European Patent No. 1651270, Minutes of the Oral Proceedings before the Opposition Division dated Mar. 17, 2010, 7 pages.
European Patent No. 1651270, Opponent's Reply to the Patentee's Grounds of Appeal dated Feb. 2011, 48 pages.
European Patent No. 1651270, Opponent's Response to Summons to Oral Proceedings, dated Jan. 14, 2010, 13 pages.
European Patent No. 1651270, Patentee's Appeal Requests, dated Sep. 28, 2010, 24 pages.
European Patent No. 1651270, Patentee's Rebuttal to Grounds of Opposition, dated May 30, 2008, 13 pages.
European Patent No. 1651270, Patentee's Response, dated Feb. 18, 2010, 7 pages.
European Patent No. 1651270, Patentee's Response to Summons to Attend Oral Proceedings dated Jul. 30, 2009, and Opponents Submission dated May 22, 2009, dated Oct. 1, 2009, 18 pages.
European Patent No. 1651270, Patentee's Submissions of Oral Proceedings, dated Jan. 15, 2010, 10 pages.
European Patent No. 1651270, Reply to Submission from Patentee dated May 30, 2008, dated May 2009, 39 pages.
European Patent No. 1763368, Opposition to European Patent No. 1763368, Patentee's Experimental Report 1, 1 page, submitted to the European Patent Office dated Jul. 28, 2010.
European Patent No. 1763368, Opposition to European Patent No. 1763368, Patentee's Experimental Report 2, 1 page, submitted to the European Patent Office dated Jul. 28, 2010.
European Patent No. 1763368, Opposition to European Patent No. 1763368, Patentee's Experimental Report 3, 8 pages, submitted to the European Patent Office dated Jul. 28, 2010.
European Patent No. 1763368, Opposition to European Patent No. 1763368, Patentee's Experimental Report 4, 6 pages, submitted to the European Patent Office dated Jul. 28, 2010.
European Patent No. 1763368, Reply to Oppositions Filed against European Patent No. 1763368, dated Jul. 26, 2010, 39 pages.
European Patent No. 1763368, Statement of Opposition by Boehringer Ingelheim Pharma GmbH & Co. KG, dated Dec. 2, 2009, 8 pages (in German).
European Patent No. 1763368, Statement of Opposition by Norton Healthcare Ltd, dated Nov. 9, 2009, 18 pages.
European Pharmacopeia 7.0 pp. 274-285 (2010).
Fenton, C. et al., "Novolizer: A Multidose Dry Powder Inhaler", Drugs, vol. 63, No. 22, 2003, 2437-2445.
Fitzgerald, M. F. et al., "Emerging trends in the COPD: bronchodilators as mono- and combination therapies," Drug Discovery Today 12(11/12): 472-478 (2007).
Food and Drug Administration, Center for Drug Evaluation and Research, "Clinical Pharmacology and Biopharmaceutics Review(s)—NDA No. 21-077", 107 pages. Available from: http://www.acessdata.fda.gov/drugsatfda_docs/nda/2000/21077_Advair%20Diskus_biopharmr.pdf.
Food and Drug Administration, Center for Drug Evaluation and Research, "Pharmacology Review(s)—NDA No. 20-831", 151 pages. Available from: http://www.acessdata.fda.gov/drugsatfda_docs/nda/2001/20831_Foradil_phrmr_P1.pdf.
Food and Drug Administration, Center for Drug Evaluation and Research, "Pharmacology Review(s)—NDA No. 20-833", 8 pages. Available from: http://www.acessdata.fda.gov/drugsatfda_docs/nda/2000/20-833_Flovent_Pharmr.pdf.
Food and Drug Administration, Pulmonary-Allergy Drugs Advisory Committee Meeting, Clinical Briefing Document, Spiriva, Sep. 6, 2002 (162 pages).
Foradil Aerolizer (formoterol fumarate) production information from Merck Product Services, downloaded May 3, 2012, from http:///www.merckservices.com/portal/site/merckproductservices/foradil/zQzWTzPzsvlzEz4.
Foye, et al., Principles of Medicinal Chemistry, 4$^{th}$ Edition, pp. 338-340 (1995).
Frijlink, HW et al., "Dry powder inhalers for pulmonary drug delivery", Expert Opinion Drug Delivery, vol. 1, No. 1, 2004, 67-86.
Frith, P. et al., "Oxitropium Bromide, Dose-Response and Time-Response Study of a New Anticholinergic Bronchodilator Drug," Chest, 1986, 89 (2), 249-253.
Fuhr et al., "Efficacy and Safety of Twice-Daily Aclidinium Bromide 400 μg Compared with Placebo and Tiotropium 18 μg QD in Moderate to Severe COPD Patients," Chest, 138(4_Meeting Abstracts): 465A; Oct. 2010.
Gao, SH et al., "Stereochemistry of the heterocyclic alcohols containing piperdine unit," Gaodeng Xuexiao Huaxue Xuebao, vol. 20: p. 232-236 (1999). (English language abstract included).
Gavalda, A. et al., "Aclidinium Bromide, A Novel Long-Acting Muscarinic Antagonist for COPD with Improved Preclinical Renal and Urinary Safety Profile," Life Sciences, 2012, 90, 301-305.

(56) References Cited

OTHER PUBLICATIONS

Gavalda, A. et al., "Aclidinium Bromide, A Novel Muscarnic Receptor Antagonist Combining Long Residence at M3 Receptors and Rapid Plasma Clearance," Oral Presentation at the European Respiratory Society Annual Congress in Stockholm, Sweden, Sep. 15-19, 2007 (13 pages).
Gavalda, A. et al., "Aclidinium Bromide, A Novel Muscarnic Receptor Antagonist Combining Long Residence at M3 Receptors and Rapid Plasma Clearance," Poster Presentation at the European Respiratory Society Annual Congress in Stockholm, Sweden, 2007, 2 pages.
Gibson, et al., "The inhibitory profile of Ibudilast against the human phosphodiesterase enzyme family," Eur. J. of Pharmacology, 538: 39-42 (1006).
Global Initiative for Asthma, Global Strategy for Asthma Management and Prevention, NIH Publication No. 02-3659, Issued Jan. 1995, revised 2002.
Global Initiative for Chronic Obstructive Lung Disease, Global Strategy for the Diagnosis, Management, and Prevention of Chronic Obstructive Pulmonary Disease, 2006.
Global Initiative for Chronic Obstructive Lung Disease, Global Strategy for the Diagnosis, Management, and Prevention of Chronic Obstructive Pulmonary Disease, National Institutes of Health, National Heart, Lung, and Blood Institute, Publication No. 2701, Mar. 2001.
Godoviko, et al., "Synthesis and Receptor Affinities of New 3-Quinuclidinyl a-Heteroaryl-aaryl-ahydroxyacetates," Journal of Pharmaceutical Sciences, 81(4): 326-329 (1992).
Godoviko, N. et al., "Synthesis and Muscarinolytic Activity of Quinuclidinyl Benzylate Iodoalkylates," Pharmaceutical Chemistry Journal, vol. 19, No. 9, pp. 602-604 (1985).
Grob, CA et al., "Die Synthese von 4-Brom- and 4-Hydroxy-Chinuclidin," Helv. Chim. Acta 41: 1184-1191 (1958).
Gras, J. et al., "Aclidinium Bromide, A Novel Long-Acting Anticholinergic Drug, has a Good Preclinical Cardiovascular Safety Profile," Published as a Poster Presentation at European Respiratory Society Annual Congress in Berlin, Germany, 2008, 2 pages.
Gras, J. et al., "The Preclinical Urinary and Renal Safety Profile of Aclidinium Bromide, A Novel Long-Acting Anticholinergic Drug," European Respiratory Society Meeting in Berlin, 2008, 1 page.
Gross, N. et al., "Dose Response to Ipratropium as a Nebulized Solution in Patients with Chronic Obstructive Pulmonary Disease, A Three-Center Study," American Review of Respiratory Disease, 1989, 139, 1188-1191.
Gross, N J. et al., "Efficacy and safety of formoterol fumarate delivered by nebulization to COPD patients", Respiratory Medicine, vol. 102, 2008, pp. 189-197.
Gross, N. et al., "Inhalation by Nebulization of Albuterol-Ipratropium Combination (Dey Combination) Is Superior to Either Agent Alone in the Treatment of Chronic Obstructive Pulmonary Disease," Respiration, 1998, 65, 354-362.
Gross, N. et al., "Role of the Parasympathetic System in Airway Obstruction Due to Emphysema," New England Journal of Medicine, 1984, 16 311 (7), 421-425.
Hansel, T. et al., Eds., An Atlas of Chronic Obstructive Pulmonary Disease, COPD, The Parthenon Publishing Group, London, 2004, ISBN 1-84214-004-3, pp. 85-89, 103, 136, 139, 140, 151-156, 168-170, 210-212.
Hansel, T. et al., Eds., New Drugs for Asthma, Allergy and COPD, Progress in Respiratory Research, Karger, Basel, 2001, 31, ISBN 3805568622, Selection Titled: Current Therapy for Asthma by P.J. Barnes, pp. 6-10.
Hardman, J. et al., Eds., Goodman and Gilman's: The Pharmacological Basis of Therapeutics, Ninth Edition, McGraw-Hill, New York, 1996, Chapter 28: Drugs Used in the Treatment of Asthma by W. Serafin, pp. 659-682.
Hardman, J. et al., Eds., Goodman and Gilman's: The Pharmacological Basis of Therapeutics, Tenth Edition, McGraw-Hill, New York, 2001, ISBN 0-07-135469-7, Chapter 10: Catecholamines, Sympathomimetic Drugs, and Adrenergic Receptor Antagonists by B. B. Hoffman, pp. 215-232.
Hardman, J. et al., Eds., Goodman and Gilman's: The Pharmacological Basis of Therapeutics, Tenth Edition, McGraw-Hill, New York, 2001, ISBN 0-07-135469-7, Chapter 28: Drugs Used in the Treatment of Asthma by B.J. Undem et al., pp. 733-754.
Hardman, J. et al., Eds., Goodman and Gilman's: The Pharmacological Basis of Therapeutics, Tenth Edition, McGraw-Hill, New York, 2001, ISBN 0-07-135469-7, Chapter 3: Principles of Therapeutics by A.S. Nies, pp. 45-66.
Hardman, J. et al., Eds., Goodman and Gilman's: The Pharmacological Basis of Therapeutics, Tenth Edition, McGraw-Hill, New York, 2001, ISBN 0-07-135469-7, Chapter 7: Muscarinic Receptor Agonists and Antagonists by J.H. Brown et al., pp. 155-173.
Hancox, RJ et al., "Randomised trial of an inhaled B2 agonist, inhaled corticosteroids and their combination in the treatment of asthma," Thorax, 54: 482-487 (1999).
Heacock, RA et al., "Materials and Methods," The Annals of Applied Biology, Marsh RW and Thomas, I, eds, Cambridge at the University Press, vol. 46, pp. 356-366 (1958).
Hele, D., "New Approaches to the Modulation of Inflammatory Processes in Airway Disease Models: ATS 2001, May 18-23, San Francisco," Respiratory Research, 2001, 2 (5), E003, 4 pages.
Huang, et al., "Preferential inhibition of human phosphodiesterase 4 by ibudilast," Life Sciences, 78:2663-2668 (1006).
India Patent No. 244472, Opposition Affidavit of Dr. S. G. Deshpande, dated Jun. 5, 2012, 17 pages.
Instructions for Medicine, The Merck Manual, M., "MIR", 1997, vol. 2, p. 693. (English translation also attached).
International Search Report for International Application No. PCT/EP2009/001831, dated Jul. 2, 2010.
International Search Report for International Application No. PCT/EP2009/001832, dated Jul. 5, 2010.
International Search Report of International Application No. PCT/EP2012/056575, dated Jun. 4, 2012.
International Search Report of International Application No. PCT/EP2013/060808, dated Jul. 16, 2013.
International Search Report of International Application No. PCT/EP2013/076606, dated Jan. 22, 2014.
International Search Report dated Nov. 15, 2007, for International Application No. PCT/EP2007/006278 (WO 2008/009397 A1).
International Search Report and Written Opinion of the ISRIEP for International Application No. PCT/EP2008/000782 dated Apr. 8, 2008.
Interview Summary dated Mar. 12, 2014, in U.S. Appl. No. 12/528,267.
Introduction to Pharmacology, 2003, pp. 96 and 181-188.
Johnson, M. "Beta2-Andrenoreceptors Mechanisms of Action of Beta2-Agonists," Pediatric Respiratory Reviews, 2001, 2, 57-62.
Johnson, M., "Salmeterol," Medicinal Research Reviews, 1995, 15 (3), 225-257.
Jones et al., "Efficacy and safety of once-daily aclidinium in chronic obstructive pulmonary disease," Respiratory Research, 2011; 12: 55 (10 pages).
Jones et al., "Efficacy and safety of twice-daily aclidinium bromide in COPD patients: the ATTAIN study," *Eur. Respir. J.*, 2012; 40(4): 830-836.
Joos, G. et al., "Bronchodilatory Effects of Aclidinium Bromide, A Long-Acting Muscarinic Antagonist in COPD Patients," Respiratory Medicine, 2010, 104, 865-872.
Joos, G. et al., "Bronchodilator effects of aclidinium bromide, a novel long-acting anticholinergic, in COPD patients: a phase II study," Abstract from European Respiratory Society dated Sep. 16, 2007.
Joos, G. "Bronchodilator effects of aclidinium bromide, a novel long-acting anticholinergic in COPD patients: a phase II study," Oral Presentation, European Respiratory Society Annual Congress, Stockholm, Sweden, Sep. 15-19, 2007 (16 pages).
JOOS Poster "Bronchodilator effects of aclidinium bromide, a novel long-acting anticholinergic, in COPD patients: a phase II study," presented at the Annual Congress of the European Respiratory Society (ERS) in Stockholm, Sweden, 2007; Enlarged Figures 2(a), 2(b) and 3 of poster, 3 pages.

(56) References Cited

OTHER PUBLICATIONS

Joos GF et al., Poster "Bronchodilator effects of aclidinium bromide, a novel long-acting anticholinergic, in COPD patients: a phase II study," presented at the Annual Congress of the European Respiratory Society (ERS) in Stockholm, Sweden, 2007, 4 pages.
Joos GF et al., Poster presented at the Annual Congress of the European Respiratory Society (ERS) in Stockholm, Sweden, 2007; Printout of the ERS webpage relating to the presentation, 2 pages.
Judgment by the High Court of Justice, Chancery Division, Patents Court, Claim No. HC 07 CO 2104 Between Laboratorios Almirall S.A. and Boehringer Ingelheim International GmbH, 2009.
Kuca, K. et al., "A general method for the quaternization of N,N-dimethyl benzylamines with long chain n-alkylbromides," Journal of Applied Biomedicine, 2: 195-198 (2004).
Katzung, B., Ed., Basic and Clinical Pharmacology, Eighth Edition, McGraw-Hill, New York, 2001, ISBN 0-8385-0598-8, Chapter 20: Drugs used in Asthma by H.A. Boushey, pp. 333-349.
Kerwin, E., "Efficacy and Safety of a 12-week Treatment with Twice-daily Aclidinium Bromide in COPD Patients (ACCORD COPD I)," COPD: Journal of Chronic Obstructive Pulmonary Disease, 2012; 9(2): 90-101.
Khan, S. et al., "Effect of the Long-Acting Tachykinin NK1 Receptor Antagonist MEN 11467 on Tracheal Mucus Secretion in Allergic Ferrets," British Journal of Pharmacology, 2001, 132 (1), 189-196.
Konzett, H. et al., "Versuchsanordnung zu Untersuchungen an der Bronchialmuskulatur," Arch. Exp. Path. Pharmacol. 195: 71-74 (1940).
Korean Patent Application No. 2009-7017243, Notice of Preliminary Rejection dated Jan. 29, 2014 and English translation (10 pages). (Translation included).
Kreese, H., "Almirall: Slowly Moving Forward with Aclidinium Bromide," Oct. 15, 2008, article available at: http://www.pharmaceutical-business-review.com, 1 page.
Kuca, K. et al., "A General Method for the Quaternization of N,N-Dimethyl Benzylamines with Long Chain N-Alkylbromides," Journal of Applied Biomedicine, 2004, 2, 195-198.
Kumar, R. et al., "Inhibition of Inflammation and Remodeling by Roflumilast and Dexamethasone in Murine Chronic Asthma," The Journal of Pharmacology and Experimental Therapeutics, 2003, 307, 349-355.
Kumazawa, T et al., "Inhibitors of Acyl-CoA Cholesterol Acyltransferase 1. Synthesis and Hypocholesterolemic Activity of Dibenz[b,e]oxepin-11carboxanilides," J. Med. Chem 37(6): 804-810 (1994).
*Laboratorios Almirall S.A. v. Boehringer Ingelheim International GmbH* (2009) EWHC (CH) (Patent) HC 07 CO 2014 (Eng.) (Unpublished); Claimant's Notice of Experiments in Reply.
*Laboratorios Almirall SA v Boehringer Ingelheim International GmbH* EWHC (CH) (Patent) HC 07 Co 2104 (English); English High Court Judgment (2009).
*Laboratorios Almirall S.A. v. Boehringer Ingelheim International Gmbh* (2009) EWHC (CH) (Patent) HC 07 CO 2104 (Eng.) (Unpublished); Declaration from Dr. Ramon Basser confirming the availability of D2 and D3, dated Dec. 13, 2007.
*Laboratorios Almirall S.A. v. Boehringer Ingelheim International Gmbh* (2009) EWHC (CH) (Patent) HC 07 CO 2104 (Eng.) (Unpublished); First Expert Report of Clive Peter Page dated Oct. 3, 2008.
*Laboratorios Almirall S.A. v. Boehringer Ingelheim International Gmbh* (2009) EWHC (CH) (Patent) HC 07 CO 2104 (Eng.) (Unpublished); First Expert Report of John Francis Costello dated Oct. 3, 2008.
*Laboratorios Almirall S.A. v. Boehringer Ingelheim International Gmbh* (2009) EWHC (CH) (Patent) HC 07 CO 2104 (Eng.) (Unpublished); First Expert Report of Professor Johan Zaagsma dated Sep. 30, 2008, statistical analysis of 90-180 minute timeframe, calculation of confidence interval for differences between AUC of measured effects of the combination and calculated sum (p value) according to (b) and (c) method analysis; and heart rate data.
*Laboratorios Almirall S.A. v. Boehringer Ingelheim International Gmbh* (2009) EWHC (CH) (Patent) HC 07 CO 2104 (Eng.) (Unpublished); First Expert Report of Professor Peter John Barnes, dated Sep. 29, 2008.
*Laboratorios Almirall S.A. v. Boehringer Ingelheim International Gmbh* (2009) EWHC (CH) (Patent) HC 07 CO 2104 (Eng.) (Unpublished); Opponent's Experimental Report 2.
*Laboratorios Almirall S.A. v. Boehringer Ingelheim International Gmbh* (2009) EWHC (CH) (Patent) HC 07 CO 2104 (Eng.) (Unpublished); Second Expert Report of Clive Peter Page dated Oct. 27, 2008, and statistical analysis of Boehringer Experiment.
*Laboratorios Almirall S.A. v. Boehringer Ingelheim International Gmbh* (2009) EWHC (CH) (Patent) HC 07 CO 2104 (Eng.) (Unpublished); Second Expert Report of John Francis Costello dated Oct. 23, 2008.
*Laboratorios Almirall S.A. v. Boehringer Ingelheim International Gmbh* (2009) EWHC (CH) (Patent) HC 07 CO 2104 (Eng.) (Unpublished); Second Expert Report of Professor Peter John Barnes dated Oct. 27, 2008.
*Laboratorios Almirall S.A. v. Boehringer Ingelheim International Gmbh* (2009) EWHC (CH) (Patent) HC 07 CO 2104 (Eng.) (Unpublished); Third Expert Report of Clive Peter Page dated Nov. 7, 2008.
*Laboratorios Almirall S.A. v. Boehringer Ingelheim International Gmbh* (2009) EWHC (CH) (Patent) HC 07 CO 2104 (Eng.) (Unpublished); Witness Statement of Ramon Basser dated Oct. 1, 2008.
*Laboratorios Almirall S.A. v. Boehringer Ingelheim International Gmbh* (2009) EWHC (CH) (Patent) HC 07 CO 2104 (Eng.) (Unpublished); Third Expert Report of Professor Johan Zaagsma dated Nov. 4, 2008.
*Laboratorios Almirall S.A. v. Boehringer Ingelheim International Gmbh* (2009) EWHC (CH) (Patent) HC 07 CO 2104 (Eng.) (Unpublished); Opponent's Experimental Report 1.
*Laboratorios Almirall S.A. v. Boehringer Ingelheim International Gmbh* (2009) EWHC (CH) (Patent) HC 07 CO 2104 (Eng.) (Unpublished); Second Expert Report of Professor Johan Zaagsma dated Oct. 27, 2008.
*Laboratorios Almirall S.A. v. Boehringer Ingelheim International Gmbh* (2009) EWHC (CH) (Patent) HC 07 CO 2104 (Eng.) (Unpublished); Witness Statement of Thierry Benoit Bouyssou, dated Sep. 30, 2008.
Larsson, K et al., "Aspects on pathophysiological mechanisms in COPD," Journal of Internal Medicine, 262; 311-340 (2007).
Larsson, L et al., "The Hydrogen Bond Condition in Some Anticholinergic Esters of Glycolic Acids I," Acta. Pharma. Suec. 11(3): 304-308 (1974).
Le Souef, P, "The meaning of lung dose", Allergy, vol. 54, 1999, pp. 93-96.
Letter dated Jun. 6, 2008, from Powell Gilbert LLP to Bristows regarding HC07 C02104, 6 pages.
Littner, M. et al., "Long-Acting Bronchodilation with Once-Daily Dosing of Tiotropium (Spiriva) in Stable Chronic Obstructive Pulmonary Disease," Am J Respir Crit Care Med, vol. 161, 2000, pp. 1136-1142.
Lopez-Vidiero, M. et al., "Effect of Atropine on Sputum Production," Thorax, 1975, 30, 543-547.
Lötvall, J. et al. "Similar bronchodilation with formoterol delivered by Aerolizer or Turbuhaler", Can Respir J., vol. 6, No. 5., Oct. 1999, pp. 412-416.
Lu, S. et al., "An Oral Selective M3 Cholinergic Reactor Antagonist in COPD," Eur Respir J. 28:772-780 (2006).
Lund, H. et al., "Quaternization Reactions," Acta Chemica Scandinavica, 1973, 27, 383-390.
Lygo, B. et al., "Asymmetric Approaches to 2-Hydroxymethylquinuclidine Derivatives," Tetrahedron, 1999, 55, 2795-2810.
Maesen, F.P.V. et al., "Ba 679 Br, A New Long-Acting Antimuscarinic Bronchodilator: A Pilot Dose-Escalation Study in COPD," European Respiratory Journal, 1993, 6, 1031-1036.
Magnussen, H. et al., "Peak inspiratory flow through the Genuair® inhaler in patients with moderate or severe COPD," Respiratory medicine, Bailliere Tindall, London, GB, vol. 103, No. 12, pp. 1832-1837 (2009).

(56) References Cited

OTHER PUBLICATIONS

Maltais et al., "Aclidinium bromide improves exercise endurance and lung hyperinflation in patients with moderate to severe COPD," Respiratory Medicine, vol. 105, No. 4, pp. 580-587 (2011) (Abstract).

Mashkovskiy, M.D., Medicaments, Moscow, Navaya Volna, 2001, p. 11.

Martin, L. "Drugs for Asthma/COPD—A Medical Primer for Physicians," http://www/lakesidepress.com/pulmonary/Asthma-Rx.html (updated Feb. 1999).

Matera, M. et al., "Ultra-Long-Acting 2-Adrenoceptor Agonists," Drugs, 2007,67 (4), 503-515.

May, EL et al., "Studies in the Anthracene Series V. A Novel Rearrangement in the Reaction of Halomethyl Ketones with Secondary Amines," J. Am. Chem. Soc. 70: 1077-1079 (1948).

Medical Dictionary, Edited by Ishiyaku Shuppan KK, 2001, p. 1554.

Merck Manual, "Chronic Obstructive Airway Disorders," 17th Edition, p. 565—(1999).

Merck Manual Home Edition article titled "Severe Acute Respiratory (SARS)," 2 pages, accessed Jul. 11, 2007.

Merck Manual Home Edition articles titled "Bronchopulmonary Dysplasia (BPD)," 2 pages; "Langerhans' Cell Granulomatosis," 2 pages; "Respiratory Tract Infections," 3 pages; "Pulmonary Embolism," 5 pages; and "Lung Cancer" 5 pages; accessed May 14, 2007.

Merck Manual of Diagnosis and Therapy, Robert Berkow ed., 16th Edition, p. 646-657 (1992).

Mery, P-F. et al., "Muscarinic Regulation of the L-Type Calcium Current in Isolated Cardiac Myocytes," Life Sciences, 1997, 60 (13-14), 1113-1120.

Meyers, AI et al., "Resolution of a-Substituted Mandelic Acids via Chiral Oxazolines Using Pressurized Chromatography," J. Org. Chem. 45(14): 2912-2914(1980).

Mikhailov, I.B., Desk of the Physician for clinical pharmacology, St. Petersburg, 2001, pp. 424-425, 439-440.

Miller, J. et al., "Standardisation of spirometry," Eur Respir J, 2005; 26: 319-338.

Mintzer, J. et al., "Anticholinergic Side-Effects of Drugs in Elderly People," Journal of the Royal Society of Medicine, 2000, 93 (9), 457-462.

Miralpeix, M. et al., "Assessment of the potency and duration of action of aclidinium bromide in guinea pig isolated trachea in vitro"; Eur Respir J., vol. 30, 2007, pp. 354s-357s, Abstract P2159.

Miralpeix, M. et al., "Assessment of the potency and duration of action of aclidinium bromide in guinea pig isolated trachea in vitro," Poster Presentation, European Respiratory Society Annual Congress, Stockholm, Sweden, Sep. 15-19, 2007 (1 page).

Miralpeix, M. et. al., "The Inhaled Anticholinergic Agent, Aclidinium Bromide, Reverses Cholinergic-Induced Bronchoconstriction in Guinea Pigs with a Fast Onset of Action and a Long Duration of Effect," Published as a Poster Presentation at the European Respiratory Society Annual Congress, Berlin, Germany, 2008 (2 pages).

Molfino, "Drugs in Clinical Development for Chronic Obstructive Pulmonary Disease," Respiration, vol. 72, No. I, 2005, pp. 105-112.

Montero, J. et al., "Effect of Aclidinium Bromide, A Novel Long-Acting Anticholinergic, on Salivation, Colonic Motility and Faecal Output in Different Animal Models," European Respiratory Society Meeting in Berlin, 2008, 1 page.

Murray, J. et al., Eds., Textbook of Respiratory Medicine, Third Edition, W.B. Saunders Company, Philadelphia, 2000, ISBN 0-7216-7711-8, Chapter 10: Respiratory Pharmacology by P.J. Barnes, pp. 231, 232, 252-265.

Murray, J. et al., Eds., Textbook of Respiratory Medicine, Third Edition, W.B. Saunders Company, Philadelphia, 2000, ISBN 0-7216-7711-8, Chapter 11: Airway Pharmacology by P.J. Barnes, pp. 267-296.

Murray, J. et al., Eds., Textbook of Respiratory Medicine, Third Edition, W.B. Saunders Company, Philadelphia, 2000, ISBN 0-7216-7711-8, Chapters 11 and 38, pp. 267-296 and 1187-1245.

Murray, J. et al., Eds., Textbook of Respiratory Medicine, Third Edition, W.B. Saunders Company, Philadelphia, 2000, ISBN 0-7216-7711-8, Chapter 38: Chronic Bronchitis and Emphysema by C.A. Piquette, pp. 1187-1245.

Murray, J. et al., Eds., Textbook of Respiratory Medicine, Third Edition, W.B. Saunders Company, Philadelphia, 2000, ISBN 0-7216-7711-8, Chapter 39: Asthma by H.A. Boushey et al., pp. 1247-1289.

National Sleep Foundation, "Asthma and Sleep," http://www.sleepfoundation.org/article/sleep-topics/asthma and sleep, (2011).

National Sleep Foundation, "COPD and Difficulty Breathing," http:/www.sleepfoundation.org/article/sleep-related-problems/chronic-obstructive-pulmonarydisease-and-sleep, (2009).

Nishikawa, M. et al., "Effect of Short- and Long-Acting 2-Adrenoceptor Agonists on Pulmonary 2-Adrenoceptor Expression in Human Lung," European Journal of Pharmacology, 1996, 318, 123-129.

Nishimura, et al., "Additive effect of oxitropium bromide in combination with inhaled corticosteroids in the treatment of elderly patients with chronic asthma," Allerology International 48: 85-88 (1999).

Noronha-Blob, L. et al., "Stereoselective Antimuscarinic Effects of 3-Quinuclidinyl Atrolactate and 3-Quinuclidinyl Xanthene-9-carboxylate," European Journal of Pharmacology, 1992, 211 (1), 97-103.

Notice of Allowance dated Mar. 30, 2005 in U.S. Appl. No. 10/740,264.

Notice of Allowance dated Dec. 21, 2005 in U.S. Appl. No. 11/116,777.

Notice of Allowance dated Jan. 9, 2007 in U.S. Appl. No. 11/324,919.

Notice of Allowance dated Sep. 13, 2006 in U.S. Appl. No. 11/325,059.

Notice of Allowance dated Nov. 23, 2007 in U.S. Appl. No. 11/636,181.

Notice of Allowance dated Feb. 26, 2010, in U.S. Appl. No. 12/074,929.

Notice of Allowance dated Jun. 23, 2011 in U.S. Appl. No. 12/374,185.

Notice of Allowance dated Jan. 10, 2011 in U.S. Appl. No. 12/787,772.

Notice of Allowance dated Oct. 20, 2011, in U.S. Appl. No. 13/011,131.

Notice of Allowance dated Sep. 16, 2015, in U.S. Appl. No. 13/672,893.

Notice of Allowance dated May 11, 2017, in U.S. Appl. No. 15/161,531.

Notice of Allowability dated Jul. 10, 2017, in U.S. Appl. No. 15/161,531.

Notice of Allowanced dated Jan. 18, 2018, in U.S. Appl. No. 13/692,032.

Notification of the Preliminary Research Report for FR 0505473 dated Dec. 12, 2005, 5 pages.

Notification of the Research Report for BE 200500268 dated Nov. 3, 2005, 5 pages.

Notification of the Transmittal of the International Search Report and the Written Opinion of the International Searching Authority, or the Declaration for International Application No. PCT/EP2005/005836 dated Aug. 10, 2005, 14 pages.

Notification of the Transmittal of the International Search Report and the Written Opinion of the International Searching Authority, or the Declaration for International Application No. PCT/EP2005/005837 dated Aug. 4, 2005, 14 pages.

Notification of the Transmittal of the International Search Report and the Written Opinion of the International Searching Authority, or the Declaration for International Application No. PCT/EP2005/005838 dated Aug. 17, 2005, 14 pages.

Notification of the Transmittal of the International Search Report and the Written Opinion of the International Searching Authority, or the Declaration for International Application No. PCT/EP2005/005839 dated Aug. 5, 2005, 14 pages.

Notification of the Transmittal of the International Search Report and the Written Opinion of the International Searching Authority, or the Declaration for International Application No. PCT/EP2005/005840 dated Aug. 17, 2005, 14 pages.

(56) References Cited

OTHER PUBLICATIONS

Notification of the Transmittal of the International Search Report and the Written Opinion of the International Searching Authority, or the Declaration for International Application No. PCT/EP2005/005841 dated Aug. 8, 2005, 14 pages.
Nyberg, K. et al., "Investigations of Dithienylglycolic Esters," Acta. Chem. Scand. 24: 1590-1596 (1970).
Office Action dated Apr. 22, 2004 in U.S. Appl. No. 10/740,264.
Office Action dated Jul. 22, 2004 in U.S. Appl. No. 10/740,264.
Office Action dated Oct. 2, 2007 in U.S. Appl. No. 10/892,033.
Office Action dated Aug. 24, 2015, in U.S. Appl. No. 13/692,032.
Office Action dated Dec. 30, 2014, in U.S. Appl. No. 13/692,032.
Office Action dated Feb. 9, 2017, in U.S. Appl. No. 13/692,032 (18 pages).
Office Action dated Jun. 2, 2014, in U.S. Appl. No. 13/692,032.
Office Action dated May 20, 2016, in U.S. Appl. No. 13/692,032.
Office Action dated Sep. 19, 2005 in U.S. Appl. No. 11/116,777.
Office Action dated Mar. 14, 2006 in U.S. Appl. No. 11/325,059.
Office Action dated Apr. 28, 2006 in U.S. Appl. No. 11/324,919.
Office Action dated Jul. 6, 2007 in U.S. Appl. No. 11/636,181.
Office Action dated Mar. 4, 2009 in U.S. Appl. No. 12/074,929.
Office Action dated Oct. 7, 2009 in U.S. Appl. No. 12/074,929.
Office Action dated Oct. 13, 2010, in U.S. Appl. No. 12/374,185.
Office Action dated Sep. 28, 2011, in U.S. Appl. No. 12/528,267.
Office Action dated Mar. 13, 2012, in U.S. Appl. No. 12/582,267.
Office Action dated Sep. 23, 2013 in U.S. Appl. No. 12/528,267.
Office Action dated Jun. 6, 2014, in U.S. Appl. No. 12/528,267.
Office Action dated Oct. 19, 2010, in U.S. Appl. No. 12/787,772.
Office Action dated Dec. 13, 2011 in U.S. Appl. No. 12/921,892.
Office Action dated May 11, 2012 in U.S. Appl. No. 12/921,892.
Office Action dated Jan. 26, 2012 in U.S. Appl. No. 12/921,921.
Office Action dated Jun. 4, 2012, in U.S. Appl. No. 12/921,921.
Office Action dated Apr. 15, 2011, in U.S. Appl. No. 13/011,131.
Office Action dated Apr. 18, 2013, in U.S. Appl. No. 13/672,893.
Office Action dated Jul. 16, 2013, in U.S. Appl. No. 13/672,893.
Office Action dated Jan. 29, 2014, in U.S. Appl. No. 13/672,893.
Office Action dated Oct. 6, 2014, in U.S. Appl. No. 13/672,893.
Office Action dated Apr. 2, 2015, in U.S. Appl. No. 14/111,211.
Office Action dated Nov. 24, 2015, in U.S. Appl. No. 14/111,211.
Office Action dated Jul. 20, 2016, in U.S. Appl. No. 14/403,220.
Office Action dated Feb. 15, 2017, in U.S. Appl. No. 14/561,857 (13 pages).
Office Action dated Nov. 20, 2017, in U.S. Appl. No. 14/561,857.
Office Action dated Jan. 29, 2016, in U.S. Appl. No. 14/652,817.
Office Action dated Oct. 18, 2016, in U.S. Appl. No. 15/161,531.
Office Action dated Aug. 18, 2016, in U.S. Appl. No. 15/218,391.
Office Action dated May 4, 2017 in U.S. Appl. No. 15/409,741.
Office Action dated Dec. 28, 2017, in U.S. Appl. No. 15/436,178.
Page, C. et al., Integrated Pharmacology, Second Edition, Mosby, Edinburgh, 2002, ISBN 0 7234 3221 X, Chapter 19: Drugs and the Pulmonary System.
Parfitt, K., Ed., Martindale: The Complete Drug Reference, Thirty-Second Edition, 1999, 745-747.
Parfitt, K., Ed., Martindale: The Complete Drug Reference, Thirty-Second Edition, 1999, 745-775.
Peretto, I. et al., "Medicinal Chemistry and Therapeutic Potential of Muscarinic M3 Antagonists," Medicinal Research Reviews, 2009, published online in Wiley InterScience, DOI 10.1002/med.20158, 36 pages.
Pharmacology Manual, Edited by KK Nanzando, 2002, pp. 20 and 23.
Pokrzywinski, RF et al. "Development and psychometric assessment of the COPD and Asthma Sleep Impact Scale (CASIS)," Health and Quality of Life Outcomes, 2009, 7:98.
Prat et al., "Discovery of Novel Quaternary Ammonium Derivatives of (3R)-Quinuclidinol Esters as Potent and Long-acting Muscarinic Antagonists with Potential for Minimal Systemic Exposure after Inhaled Administration . . . ", J. Med Chem: Aug. 27, 2009; 52(16), pp. 5076-5092.

Puddicombe, S. et al., "Involvement of the Epidermal Growth Factor Receptor in Epithelial Repair in Asthma," The FASEB Journal, 2000, 14, 1362-1374.
Rabe, et al., "Roflumilast—an oral anti-inflammatory treatment for chronic obstructive pulmonary disease: a randomized controlled trial," Lancet, 366: 563-571 (Aug. 13, 2005).
Rang, H et al., Eds., Pharmacology, Third Edition, 1995, Chapter 17, "The Respiratory System," pp. 351-366.
Rang, HP et al., "Pharmacology," Churchill Livingston Inc., pp. 358-361 (1995).
Rees, PJ "Bronchodilators in the therapy of chronic obstructive pulmonary disease," Eur. Respir. Mon. 7:135-149 (1998).
Restriction Requirement dated Jan. 25, 2016, in U.S. Appl. No. 14/403,220.
Restriction Requirement dated Jan. 28, 2014, in U.S. Appl. No. 13/692,032.
Restriction Requirement dated Apr. 7, 2016, in U.S. Appl. No. 14/561,857.
Rennard, SI, (1997) "Anticholinergics and beta2-agonists: Efficacy, Safety and Combination Therapy in Chronic Obstructive Pulmonary Disease," Chapter 9, Barnes and Buist (Ed.) The Role of Anticholinergics in Chronic Obstructive Pulmonary Disease and Chronic Asthma, pp. 137-144, Gardiner-Caldwell Communications Limited.
Reynolds, J., Ed., Martindale: The Extra Pharmacopoeia, Twenty-ninth Edition, 1998, 522.
Rigaudy, J et al., "Cetones Derivees du Dibzeno [a,d]cycloheptadiene. La Dibenzo-2,3-6,7 Cycloheptadienedione-4,5" Bull. Soc. Chim. France, 638-643 (1959).
Ringdahl, R. et al., "Facile Preparation of the Enantiomers of 3-Acetoxyquinuclidinol," Acta Pharm Suec. 16: 281-283 (1979).
Rochester, C., Ed., Clinics in Chest Medicine, W.B. Saunders Company, Philadelphia, 2000, 21 (4), ISSN 0272-5231, Selection Titled: Update on Pharmacologic Therapy for Chronic Obstructive Pulmonary Disease by G. Ferguson, pp. 723-738.
Romain, O. et al., "Actualities Pharmaceutiques," (2006) 1596-1596, 13(12), XP02799707, ISSN: 0929-693X, DOI: 10 1016/J. ARCPED Sep. 19, 2006. Archives De Pediatrie, Elsevier, Paris FR.
Rucinski, T. et al., Reuters, "Almirall Seen Likely to Repeat Lung Drug Trial," Oct. 14, 2008, article available at: http://money.aol.ca/article/almirall-seen-likely-to-repeat-lung-drug-trial/379398, 1 page.
Ryder, H, "Discovery of aclidinium bromide: A new long acting muscarinic antagonist for COPD," Oral Presentation, International Symposium on Advances in Synthetic and Medicinal Chemistry, Saint Petersburg, Russia, Aug. 27-31, 2007 (33 pages).
Rzeszotarski, W. et al., "Affinity and Selectivity of the Optical Isomers of 3-Quinuclidinyl Benzilate and Related Muscarinic Antagonists," Journal of Medicinal Chemistry, 1988, 31, 1463-1466.
Schelfhout, V. et al., "Activity of LAS 34273, A New Long Acting Anticholinergic Antagonist, in COPD Patients," American Thoracic Society, 2003, 99th International Conference, Abstract No. A319.
Schelfhout, V. et al., "Activity of LAS 34273, A New Long Acting Anticholinergic Antagonist, in COPD Patients," Poster, ATS 2003—99th International Conference, May 2003 and Expanded Version, 4 pages.
Schelfhout, V. et al., "Activity of LAS 34273, A New Long Acting Anticholinergic Antagonist," American Thoracic Society, 2003, 99th International Conference, Abstract No. A93.
Schelfhout, V. et al., "Activity of LAS 34273, A New Long Acting Anticholinergic Antagonist," Poster, ATS 2003—99th International Conference, May 2003 and Expanded Version, 4 pages.
Schelfhout, V et al., "Bronchodilator/bronchoprotective effects of aclidinium bromide, a novel long-acting anticholinergic: a phase I study", Eur Respir J., vol. 30, 2007; pp. 354s-357s, Abstract P2146.
Schelfhout, V et al., "Bronchodilator/bronchoprotective effects of aclidinium bromide, a novel long-acting anticholinergic: a phase I study," Poster Presentation, European Respiratory Society Annual Congress, Stockholm, Sweden, Sep. 15-19, 2007 (1 page).
Schelfhout, VJ et al., "Activity of LAS 34273," A New Long Acting Anticholinergic Antagonist in COPD Patients, poster, ATS 2003—99th International Conference, May 2003.
Schelfhout, VJ et al., "Activity of LAS 34273," A New Long Acting Anticholinergic Antagonist, ATS 2003—99th International Conference, May 2004.

(56) References Cited

OTHER PUBLICATIONS

Schmidt, R. "Dose-Finding Studies in Clinical Drug Development," Eur J Clin Pharmacol. 1988. 34:15-19.
Sciurba et al., Am J Respir Crit Care Med, 2011; 183: A1589 (Abstract).
Search Report for Application No. CY 3405, Date of completion of the search Jun. 28, 2006, 5 pages.
Search Report for Patent Application No. 1029151, dated Feb. 14, 2006, 5 pages.
Sentellas et al., "Aclidinium Bromide, a New, Long-acting, Inhaled Muscarinic Antagonist: in vitro Plasma Inactivation and Pharmacological Activity of its Main Metabolites": Eur J Pharm Sci: Mar. 18, 2010; 1 page, Abstract only.
Sentellas, S. et al., "Aclidinium Bromide, A New, Long-Acting, Inhaled Muscarinic Antagonist: In vitro Plasma Inactivation and Pharmacological Activity of Its Main Metabolites," European Journal of Pharmaceutical Sciences, 2010, 39, 283-290.
Serafin, W. "Drugs Used in the Treatment of Asthma," Goodman Gilman's The Pharmacological Basis of Therapeutics, Chapter 28, Joel G. Hardman et al eds, 9th Edition, p. 659-682 (1996).
Sestanj, K. "A Facile Formation of Dibenzo[a,b] cycloheptenylium Ion by Decarbonylation Color Reactions of the Cyheptaminde Metabolites," Can. J. Chem. 49: 664-665 (1971).
Sharma, V. et al. "Does Mammalian Heart Contain Only the M2-Muscarinic Receptor Subtype?" Life Sciences, 1997, 60 (13-14), 1023-1029.
Singh, D. et al., "A randomised, placebo- and active-controlled dose-finding study of aclidinium bromide administered twice a day in COPD patients," Pulm Pharmacol Ther. Apr. 2013;26(2):305. Abstract only.
Singh, D. et al., "A randomised, placebo- and active-controlled dose-finding study of aclidinium bromide administered twice a day in COPD patients," Pulm Pharmacol Ther. Apr. 2013;26(2):305. Corrigendum.
Singh, D. et al., "A randomised, placebo- and active-controlled dose-finding study of aclidinium bromide administered twice a day in COPD patients," Pulm Pharmacol Ther (2012) 25(3) 2012 248-253.
Singh, D. et al., "Corrigendum to 'A randomised, placebo- and active-controlled dose-finding study of aclidinium bromide administered twice a day in COPD patients' [Pulm Pharmacol Ther 25(3) 2012 248-253]," Pulm Pharmacol Ther. Apr. 2013;26(2):305.
Singh, D. et al., "Efficacy and safety of aclidinium bromide/formoterol fumarate fixed-dose combinations compared with individual components and placebo in patients with COPD (ACLIFORM—COPD): a multicentre, randomized study," BMC Pulmonary Medicine, 2014, 14:178, 11 pages.
Spirva® Handhihaler® Prescribing Information, Boehringer Ingelheim International GmbH, 59873/US/2, Sep. 2004.
Spiriva Prescribing Information published 2004.
Spiriva Pharmacology Reviews, Part 1, 47 pages, http://www.accessdata.fda.gov/drugsatfda_docs/nda/2004/21-395_Spiriva.cfm, website last accessed Mar. 6, 2014.
Spiriva Pharmacology Reviews, Part 2, 47 pages, retrieved Jul. 31, 2015, from http://www.accessdata.fda.gov/drugsatfda_docs/nda/2004/21-395.pdf_Spiriva_Pharmr_P2.pdf.
Spiriva Pharmacology Reviews, Part 3, 47 pages, retrieved Jul. 31, 2015, from http://www.accessdata.fda.gov/drugsatfda_docs/nda/2004/21-395.pdf_Spiriva_Pharmr_P3.pdf.
Spiriva Pharmacology Reviews, Part 4, 47 pages, retrieved Jul. 31, 2015, from http://www.accessdata.fda.gov/drugsatfda_docs/nda/2004/21-395.pdf_Spiriva_Pharmr_P4.pdf.
Spiriva Pharmacology Reviews, Part 5, 47 pages, retrieved Jul. 31, 2015, from http://www.accessdata.fda.gov/drugsatfda_docs/nda/2004/21-395.pdf_Spiriva_Pharmr_P5.pdf.
Spiriva Pharmacology Reviews, Part 6, 46 pages, retrieved Jul. 31, 2015, from http://www.accessdata.fda.gov/drugsatfda_docs/nda/2004/21-395.pdf_Spiriva_Pharmr_P6.pdf.
Spitzer, W. et al., "The Use of P-Agonists and the Risk of Death and Near Death from Asthma," New England Journal of Medicine, 1992, 326, 501-506.
Steckel, H. et al., "Functionality testing of inhalation grade lactose", European Journal of Pharmaceutics and Biopharmaceutics, vol. 57, 2004, 495-505.
Suissa, S. et al., "Patterns of Increasing P-Agonist Use and the Risk of Fatal or Near-Fatal Asthma," European Respiratory Journal, 1994, 7, 1602-1609.
Summary of Product Characteristics (SmPC) for "Duaklir Genuair 340 micrograms/12 micrograms inhalation powder", 35 pages.
Summary of Product Characteristics (SmPC) for "Eklira Genuair 322 micrograms inhalation powder", 36 pages.
Tavakkoli et al., "Drug Treatment of Asthma in the 1990s, Achievements and New Strategies," Drugs, 57(1): 1-8 (1999).
Teixera et al., "Phosphodiesterase (PDE) 4 inhibitors: anti-inflammatory drugs of the future," TiPS, 18:164 (May 1997).
Telko, M J et al., "Dry Powder Inhaler Formulation", Respiratory Care, vol. 50, No. 9, Sep. 2005, 1209-27.
Tennant, R. et al., "Long-Acting P2-Adrenoreceptor Agonists or Tiotropium Bromide for Patients with COPD: Is Combination Therapy Justified?" Current Opinion in Pharmacology, 2003, 3, 270-276.
The Merck Manual, "Instructions for Medicine," 1997, 2, 693 and English-language translation (4 pages).
The Merck Manual of Diagnosis and Therapy, Seventeenth Edition, 1999, Foreword and Chapter 68, "Chronic Obstructive Airway Disorders," pp. 555-583.
Theolair™ Prescribing Information, 3M Pharmaceuticals, 601000, May 1998, 12 pages.
Torphy, T. "Phosphodiesterase Isozymes, Molecular Targets for Novel Antiasthma Agents," Am. J. Respit. Crit. Care Med., 157:351-370 (1998).
Traunecker, W. et al., "Pharmacological Effects of a Combination of Fenoterol Hydrobromide and Ipratropium Bromide," Respiration, 1986, 50 (4), 244-251.
U.S: National Institute of Health, "A Trial Assessing LAS34273 in Moderate to Severe Stable Chronic Obstructive Pulmonary Disease (COPD)", updated Feb. 20, 2008, 2 pages. Available from: https://clinicaltrials.gov/archive/NCT00363896/2008_02_20.
U.S: National Institute of Health, "Efficacy and Safety of LAS34273 in Patients with Moderate to Severe Stable Chronic Obstructive Pulmonary Disease (COPD)", updated Feb. 20, 2008, 2 pages. Available from: https://clinicaltrials.gov/archive/NCT00358436/2008_02_20.
U.S. Appl. No. 10/891,552 Advisory Action dated May 24, 2007, 4 pages.
U.S. Appl. No. 10/891,552 Amendment Under 37 C.F.R. § 1.111 in Response to Apr. 11, 2006, Office Action dated Sep. 19, 2006, 15 pages.
U.S. Appl. No. 10/891,552 Amendment Under 37 C.F.R. § 1.116 in Response to Dec. 12, 2006, Final Office Action dated May 7, 2007, 16 pages.
U.S. Appl. No. 10/891,552 Examiner-Initiated Interview Summary and Notice of Abandonment dated Nov. 4, 2010, 4 pages.
U.S. Appl. No. 10/891,552 Final Office Action and Examiner-Initiated Interview Summary dated Apr. 8, 2010, 30 pages.
U.S. Appl. No. 10/891,552 Final Office Action dated Dec. 12, 2006, 15 pages.
U.S. Appl. No. 10/891,552 Final Office Action dated Jan. 7, 2009, 26 pages.
U.S. Appl. No. 10/891,552 Interview Summary dated Apr. 22, 2008, 4 pages.
U.S. Appl. No. 10/891,552 Non-Final Office Action dated Apr. 11, 2006, 18 pages.
U.S. Appl. No. 10/891,552 Non-Final Office Action dated Aug. 22, 2007, 17 pages.
U.S. Appl. No. 10/891,552 Non-Final Office Action dated May 12, 2008, 21 pages.
U.S. Appl. No. 10/891,552 Non-Final Office Action dated Aug. 17, 2009, 26 pages.
U.S. Appl. No. 10/891,552 Reply for RCE Filing dated Jun. 8, 2009, 21 pages.

(56) References Cited

OTHER PUBLICATIONS

U.S. Appl. No. 10/891,552 Reply to May 24, 2007, Advisory Action dated Jun. 1, 2007, 4 pages.
U.S. Appl. No. 10/891,552 Reply to Office Action Under 37 C.F.R. § 1.111 dated Feb. 22, 2008, 17 pages.
U.S. Appl. No. 10/891,552 Reply to Office Action Under 37 C.F.R. § 1.111 dated Oct. 13, 2008, 17 pages and Declaration of Thierry Benoit Bouyssou Under 37 C.F.R. § 1.132 dated Sep. 5, 2008, 6 pages.
U.S. Appl. No. 10/891,552 Reply to Office Action Under 37 C.F.R. § 1.111 dated Jan. 19, 2010, 15 pages.
U.S. Appl. No. 10/891,552 Supplemental Reply dated Jun. 24, 2009, 2 pages, and Declaration Under 37 C.F.R. § 1.132 dated Jun. 15, 2009, 6 pages.
U.S. Appl. No. 10/891,552 Supplemental Reply to Office Action dated Mar. 29, 2010, 15 pages.
U.S. Appl. No. 10/892,033 Advisory Action dated Jun. 3, 2010, 4 pages.
U.S. Appl. No. 10/892,033 Advisory Action dated Jan. 31, 2012, 5 pages.
U.S. Appl. No. 10/892,033 Applicant Initiated Interview Summary dated Nov. 16, 2011, 3 pages.
U.S. Appl. No. 10/892,033 Brief on Appeal Under 37 C.F.R. §41.37 dated Apr. 7, 2012, 91 pages.
U.S. Appl. No. 10/892,033 Examiner Interview Summary Record dated Nov. 17, 2010, 3 pages.
U.S. Appl. No. 10/892,033 Examiner Interview Summary Record dated Feb. 2, 2011, 8 pages.
U.S. Appl. No. 10/892,033 Examiner's Answer to Appeal Brief dated May 18, 2012, 26 pages.
U.S. Appl. No. 10/892,033 Final Office Action dated Mar. 2, 2009, 19 pages.
U.S. Appl. No. 10/892,033 Final Office Action dated Mar. 31, 2010, 18 pages.
U.S. Appl. No. 10/892,033 Final Office Action dated Sep. 19, 2011, 41 pages.
U.S. Appl. No. 10/892,033 Issue Fee dated Oct. 26, 2010, 1 page.
U.S. Appl. No. 10/892,033 Issue Fee dated Dec. 2, 2010, 4 pages.
U.S. Appl. No. 10/892,033 Non-Final Office Action dated Jul. 18, 2008, 18 pages.
U.S. Appl. No. 10/892,033 Non-Final Office Action dated Mar. 2, 2011, 32 pages.
U.S. Appl. No. 10/892,033 Non-Final Office Action dated Oct. 15, 2009, 18 pages.
U.S. Appl. No. 10/892,033 Notice of Abandonment dated Aug. 3, 2015, 3 pages.
U.S. Appl. No. 10/892,033 Notice of Allowance dated Oct. 7, 2010, 9 pages.
U.S. Appl. No. 10/892,033 Notice of Allowance dated Nov. 22, 2010, 7 pages.
U.S. Appl. No. 10/892,033 Notice of Withdrawal from Issue Branch dated Oct. 29, 2010, 1 page.
U.S. Appl. No. 10/892,033 Notice of Withdrawal from Issue Branch dated Jan. 10, 2011, 3 pages.
U.S. Appl. No. 10/892,033, Office Action Response dated Apr. 2, 2008, 18 pages.
U.S. Appl. No. 10/892,033 Patent Board Decision, Appeal 2012-009895 dated May 19, 2015, 14 pages.
U.S. Appl. No. 10/892,033 Reply After Final Rejection dated May 11, 2010, 10 pages.
U.S. Appl. No. 10/892,033 Reply After Final Rejection dated Jan. 19, 2012, 18 pages.
U.S. Appl. No. 10/892,033 Reply Brief dated Jun. 21, 2012, 5 pages.
U.S. Appl. No. 10/892,033 Reply dated Dec. 18, 2008, 27 pages.
U.S. Appl. No. 10/892,033 Reply dated Jan. 13, 2010, 8 pages.
U.S. Appl. No. 10/892,033 Reply dated Jul. 5, 2011, 21 pages.
U.S. Appl. No. 10/892,033 Reply for RCE dated Aug. 3, 2009, 19 pages.
U.S. Appl. No. 11/116,777, Amendment and Response to Office Action dated Sep. 30, 2005, 14 pages.
U.S. Appl. No. 11/409,157 Examiner Interview Summary Record dated Feb. 7, 2007, 3 pages.
U.S. Appl. No. 11/409,157 Requirement for Restriction/Election dated Nov. 16, 2006, 10 pages.
U.S. Appl. No. 11/409,157 Response to Restriction Requirement dated May 16, 2007, 7 pages.
U.S. Appl. No. 12/070,298 Examiner Interview Summary Record dated Apr. 7, 2011, 4 pages.
U.S. Appl. No. 12/787,772 Suggestion for Interference dated Nov. 23, 2010, 15 pages.
U.S. Appl. No. 12/875,601 Amendment Under 37 C.F.R. § 1.111 in Response to Jan. 26, 2015, Office Action filed Jun. 5, 2015, 19 pages.
U.S. Appl. No. 12/875,601, Appeal Brief, filed Oct. 6, 2016, 35 pages.
U.S. Appl. No. 12/875,601 Examiner's Answer to Appeal Brief dated Dec. 15, 2016, 16 pages.
U.S. Appl. No. 12/875,601 Final Office Action dated Sep. 24, 2015, 29 pages.
U.S. Appl. No. 12/875,601 Interview Summary dated Jan. 27, 2011, 4 pages.
U.S. Appl. No. 12/875,601 Non-Final Office Action dated Apr. 4, 2014, 22 pages.
U.S. Appl. No. 12/875,601 Non-Final Office Action dated Jan. 26, 2015, 26 pages.
U.S. Appl. No. 12/875,601 Reply to Office Action Under 37 C.F.R. § 1.111 dated Oct. 3, 2014, 15 pages, and Declaration of Thierry Benoit Bouyssou Under 37 C.F.R. § 1.132 dated Sep. 5, 2008, 6 pages, and Declaration Under 37 C.F.R. § 1.132 dated Jun. 15, 2009, 6 pages.
U.S. Appl. No. 12/912,145 Amendment and Response to Requirements for Restriction and Election of Species dated Dec. 4, 2013, 16 pages.
U.S. Appl. No. 12/912,145 Final Office Action dated Jul. 23, 2014, 54 pages.
U.S. Appl. No. 12/912,145 Non-Final Office Action dated Jan. 30, 2014, 40 pages.
U.S. Appl. No. 12/912,145 Notice of Abandonment dated Feb. 6, 2015, 3 pages.
U.S. Appl. No. 12/912,145 Reply dated Jun. 30, 2014, 14 pages.
U.S. Appl. No. 12/912,145 Requirement for Restriction/Election dated Nov. 4, 2013, 10 pages.
U.S. Appl. No. 13/354,873 Final Office Action dated Dec. 28, 2012, 4 pages.
U.S. Appl. No. 13/354,873 Non-Final Office Action dated Aug. 17, 2012, 8 pages.
U.S. Appl. No. 13/354,873 Notice of Allowance dated Apr. 11, 2013, 6 pages.
U.S. Appl. No. 13/939,742 Non-Final Office Action dated Sep. 6, 2013, 8 pages.
U.S. Appl. No. 13/939,742 Notice of Allowance dated Mar. 20, 2014, 8 pages.
U.S. Appl. No. 14/305,701 Applicant Initiated Interview Summary dated Jan. 22, 2016, 3 pages.
U.S. Appl. No. 14/305,701 Examiner-Initiated Interview Summary dated Mar. 2, 2017, 2 pages.
U.S. Appl. No. 14/305,701 Final Office Action dated Feb. 28, 2017, 20 pages.
U.S. Appl. No. 14/305,701 Non-Final Office Action dated May 16, 2016, 17 pages.
U.S. Appl. No. 14/305,701 Requirement for Restriction/Election dated Jul. 31, 2015, 5 pages.
U.S. Appl. No. 14/305,701 Response to Election of Species Requirement dated Feb. 1, 2016, 4 pages.
U.S. Appl. No. 14/305,701 Response to Non-Final Office Action dated Nov. 16, 2016, 126 pages.
U.S. Appl. No. 14/311,102 Non-Final Office Action dated Jul. 25, 2014, 9 pages.
U.S. Appl. No. 14/311,102 Notice of Allowance dated Feb. 10, 2015, 7 pages.
U.S. Appl. No. 14/712,866 Non-Final Office Action dated Jun. 5, 2015, 9 pages.

(56) References Cited

OTHER PUBLICATIONS

U.S. Appl. No. 14/712,866 Notice of Allowance dated Jan. 6, 2016.
U.S. Appl. No. 15/019,009 Non-Final Office Action dated Oct. 12, 2016, 26 pages.
U.S. Appl. No. 15/019,009 Notice of Allowance dated Mar. 21, 2017, 10 pages.
U.S. Appl. No. 15/095,036 Non-Final Office Action dated Aug. 2, 2016, 9 pages.
U.S. Appl. No. 15/409,741 Non-Final Office Action dated May 4, 2017, 11 pages.
U.S. Appl. No. 15/599,646 Non-Final Office Action dated Aug. 25, 2017, 11 pages.
Ueda, I. "The Rearrangement of 10-Bromo-10,11-Dihydrodibenzo[b,f]thiepin-11-one and Related Compounds in an Alkaline Solution," Bulletin of the Chemical Society of Japan, 48(4): 2306-2309 (1975).
United States Pharmacopeia, pp. 242-263 (2013).
Van Gestel, Arnoldus J. et al., "Predicting daily Physical Activity in Patients with Chronic Obstructive Pulmonary Disease," PLOS ONE, vol. 7, Issue 11, p. e48081 (2012).
Van Noord, J.A. et al., "A randomised controlled comparison of tiotropium and ipratropium in the treatment of chronic obstructive pulmonary disease," Thorax, 55: 289-294 (2000).
Van Noord, J. et al., "Comparison of Once Daily Tiotropium, Twice Daily Formoterol and the Free Combination, Once Daily, in Patients with COPD," Poster, ATS 2003—99th International Conference, May 2003, 1 page.
Van Noord, J. et al., "Tiotropium Maintenance Therapy in Patients with COPD and the 24-h Spirometric Benefit of Adding Once or Twice Daily Formoterol During 2-week Treatment Periods," Poster, ATS 2003—99th International Conference, May 2003, 1 page.
Virk, D., "Sleep disturbances in individuals diagnosed with respiratory diseases; asthma, bronchiectasis, COPD and asbestosis," European Journal of Neurology, vol. 17, No. Suppl. 3, p. 623 (2010).
Waelbroek, M. et al., "Binding of Selective Antagonists to Four Muscarinic Receptors (M1 to M4) in Rat Forebrain," Mol. Pharmacol. 38:267-273 (1990).
Walsh, D. et al., "Synthesis and Antiallergy Activity of 4-(Diarylhydroxymethyl)-1-[3-(aryloxy)propyl]piperidines and Structurally Related Compounds," Journal of Medicinal Chemistry, 1989, 32, 105-118.
Watz, H. et al., "Physical activity in patients with COPD," European Respiratory Journal, vol. 33, No. 2, pp. 262-272 (2009).
Wedzicha, J. et al., Eds., The Effective Management of Chronic Obstructive Pulmonary Disease, Aesculapius Medical Press, London, 2001, ISBN 0 903044 19 7, Chapter 3: The Importance of Achieving Diagnostic Accuracy by R.A. Stockley, pp. 21-30; Chapter 4: Current Thinking on the Nature of Exacerbation and the Time Course and Recovery of Exacerbations of COPD by J.A. Wedzicha et al., pp. 33-41.
Wedzicha, J. et al., Eds., The Effective Management of Chronic Obstructive Pulmonary Disease, Aesculapius Medical Press, London, 2001, ISBN 1 903044 19 7, Chapter 5: Scientific Evidence and Expert Clinical Opinion for the Selection and Use of Bronchodilators: Clinical Decision Making in the Individual Patient by P.S. Marino et al., pp. 43-63.
WHO Drug Information, "International Nonproprietary Names for Pharmacological Substances (INN), Recommended International Nonproprietary Names: List 57," 2007, 21 (1), 53-55.
Zaagsma, J. et al. "Muscarinic Control of Airway Function," Life Sciences, 1997, 60 (13-14), 1061-1068.
Zaagsma, J. et al., Eds., Muscarinic Receptors in Airways Disease, Birkhauser Verlag, Basel, 2001, ISBN 3-7643-5988-9, Chapter Titled: The Role of Anticholinergics in Asthma and COPD by K.R. Chapman, pp. 203-219.

\* cited by examiner

DOSAGE AND FORMULATION

This application is a continuation of U.S. patent application Ser. No. 13/692,032, filed Dec. 3, 2012, which is a continuation of U.S. patent application Ser. No. 12/921,921, having a 35 U.S.C. § 371(c) date of Oct. 5, 2010, which is a national stage filing of International Application No. PCT/EP2009/001832, filed Mar. 13, 2009, and claims priority to European Patent Application No. 08382010.0, filed Mar. 13, 2008, all of which are incorporated herein by reference.

BACKGROUND

Aclidinium bromide is 3(R)-(2-hydroxy-2,2-dithien-2-ylacetoxy)-1-(3-phenoxypropyl)-1-azoniabicyclo[2.2.2]octane bromide, described in, e.g., WO 0104118. Although this compound is known to be a long-acting anticholinergic useful in the treatment of respiratory diseases, the optimal dosage is not disclosed.

SUMMARY OF THE INVENTION

It is now surprisingly found that, for treatment of respiratory disorders, particularly asthma and COPD, in an adult human, aclidinium is most effective upon administration by inhalation in a dosage of about 400 µg metered nominal dose, typically a single dosage of about 400 micrograms per day metered nominal dose, (e.g., about 360 µg emitted dose, and about 120 µg Fine Particle dose) (weight corresponding to aclidinium bromide).

The invention thus provides in a first embodiment a pharmaceutical composition for inhalation comprising aclidinium in the form of a dry powder of a pharmaceutically acceptable salt, e.g., aclidinium bromide, in admixture with a pharmaceutically acceptable dry powder carrier, e.g., lactose particles, (i) comprising a single metered nominal dose of aclidinium equivalent to about 400 µg aclidinium bromide, or (ii) in a multidose dry powder inhaler device calibrated to provide a metered nominal dose of aclidinium equivalent to about 400 µg aclidinium bromide. This composition can be administered one or more times per day. Preferably once or twice a day.

In a second embodiment, the invention provides a method of treating a respiratory condition, e.g., selected from asthma and chronic obstructive pulmonary disease, in a patient in need of such treatment, comprising administering a dose, typically a single daily dose or twice daily dose, of aclidinium, e.g., aclidinium bromide, equivalent to about 400 µg metered nominal dose aclidinium bromide, e.g., comprising administering a pharmaceutical composition according to the previous paragraph. The invention further provides the use of aclidinium in the manufacture of a medicament, e.g., as described in the preceding paragraph, for use in such a method.

The aclidinium may be administered as monotherapy, or in combination with one or more additional anti-inflammatory and/or bronchodilating agents, e.g., corticosteroids, PDE IV inhibitors and β2-agonists, e.g., formoterol, salmeterol, budesonide, and mometasone, and the invention thus further provides methods as described above further comprising administration of an effective amount of such an agent, as well as pharmaceutical compositions as described above, further comprising such additional agent(s).

DETAILED DESCRIPTION OF THE INVENTION

Typically, the aclidinium is administered in the form of a salt with an anion X, wherein X is a pharmaceutically acceptable anion of a mono or polyvalent acid. More typically, X is an anion derived from an inorganic acid, such as hydrochloric acid, hydrobromic acid, sulphuric acid and phosphoric acid, or an organic acid such as methanesulphonic acid, acetic acid, fumaric acid, succinic acid, lactic acid, citric acid or maleic acid. Preferably the aclidinium is in the form of aclidinium bromide.

The aclidinium is preferably administered in the form of a dry powder, in admixture with a suitable carrier, e.g., lactose powder, suitable for inhalation.

For example, in one embodiment, the aclidinium is aclidinium bromide in admixture with lactose powder.

The respiratory disease or condition to be treated with the formulations and methods of the present invention is typically asthma, acute or chronic bronchitis, emphysema, chronic obstructive pulmonary disease (COPD), bronchial hyperreactivity or rhinitis, in particular asthma or chronic obstructive pulmonary disease (COPD), especially COPD.

In the context of dosage of an active agent, "about" as used herein means within the normal limits of acceptable variations as defined by the European and US Pharmacopeia of plus/minus 35% or preferably acceptable variations as defined by the current most stringent requirement, the US FDA draft guidance for inhaler of plus/minus 25% or especially within the metered dosing accuracy for the dispensing system e.g. +/−10% Thus a metered nominal dose of "about 400 µg" is meant a target dose of 400 µg subject to variation within the normal limits of acceptance for the dispensing system, e.g. plus/minus 35% (acceptable variations as defined by the European and US Pharmacopeia) or preferably 300-500 µg (or acceptable variations as defined by the current most stringent requirement, the US FDA draft guidance for inhaler) or especially 340-460 µg (or within the metered dosing accuracy of the inhaler).

The emitted dose and the fine particle dose (fine particle dose=µg aclidinium bromide in the emitted dose below a cut off aerodynamic threshold of 5 micrometer) are subjected to the same variation and proportional to the metered dose and are therefore for the emitted dose e.g. a metered nominal dose of about 400 µg (plus/minus 35%) corresponds to about 360 µg emitted dose (plus/minus 35%), and about 120 micrograms Fine Particle dose (plus/minus 35%)

Packaging of the formulation may be suitable for unit dose or multi-dose delivery. In the case of multi-dose delivery, the formulation can be pre-metered or metered in use. Dry powder inhalers are thus classified into three groups: (a) single dose, (b) multiple unit dose and (c) multi dose devices.

Formulations generally contain a powder mix for inhalation of the compounds of the invention and a suitable powder base (carrier substance) such as lactose or starch. Use of lactose is preferred. Each capsule or cartridge may generally contain between 2 µg and 400 µg of each therapeutically active ingredient. Alternatively, the active ingredient (s) may be presented without excipients.

For single dose inhalers of the first type, single doses have been weighed by the manufacturer into small containers, which are mostly hard gelatine capsules. A capsule has to be taken from a separate box or container and inserted into a receptacle area of the inhaler. Next, the capsule has to be opened or perforated with pins or cutting blades in order to allow part of the inspiratory air stream to pass through the capsule for powder entrainment or to discharge the powder from the capsule through these perforations by means of centrifugal force during inhalation. After inhalation, the emptied capsule has to be removed from the inhaler again. Mostly, disassembling of the inhaler is necessary for inserting and removing the capsule, which is an operation that can be difficult and burdensome for some patients. Other drawbacks related to the use of hard gelatine capsules for inhalation powders are (a) poor protection against moisture uptake from the ambient air, (b) problems with opening or perforation after the capsules have been exposed previously to extreme relative humidity, which causes fragmentation or indenture, and (c) possible inhalation of capsule fragments. Moreover, for a number of capsule inhalers, incomplete expulsion has been reported.

Some capsule inhalers have a magazine from which individual capsules can be transferred to a receiving chamber, in which perforation and emptying takes place, as described in WO 92/03175. Other capsule inhalers have revolving magazines with capsule chambers that can be brought in line with the air conduit for dose discharge (e. g. WO91/02558 and GB 2242134). They comprise the type of multiple unit dose inhalers together with blister inhalers, which have a limited number of unit doses in supply on a disk or on a strip.

Blister inhalers provide better moisture protection of the medicament than capsule inhalers. Access to the powder is obtained by perforating the cover as well as the blister foil, or by peeling off the cover foil. When a blister strip is used instead of a disk, the number of doses can be increased, but it is inconvenient for the patient to replace an empty strip. Therefore, such devices are often disposable with the incorporated dose system, including the technique used to transport the strip and open the blister pockets.

Multi-dose inhalers do not contain pre-measured quantities of the powder formulation. They consist of a relatively large container and a dose measuring principle that has to be operated by the patient. The container bears multiple doses that are isolated individually from the bulk of powder by volumetric displacement. Various dose measuring principles exist, including rotatable membranes (e. g. EP0069715) or disks (e. g. GB 2041763; EP 0424790; DE 4239402 and EP 0674533), rotatable cylinders (e. g. EP 0166294; GB 2165159 and WO 92/09322) and rotatable frustums (e. g. WO 92/00771), all having cavities which have to be filled with powder from the container. Other multi dose devices have measuring slides (e.g. U.S. Pat. No. 5,201,308 and WO 97/00703) or measuring plungers with a local or circumferential recess to displace a certain volume of powder from the container to a delivery chamber or an air conduit e. g. EP 0505321, WO 92/04068 and WO 92/04928.

Reproducible dose measuring is one of the major concerns for multi dose inhaler devices. The powder formulation has to exhibit good and stable flow properties, because filling of the dose measuring cups or cavities is mostly under the influence of the force of gravity. For reloaded single dose and multiple unit dose inhalers, the dose measuring accuracy and reproducibility can be guaranteed by the manufacturer. Multi dose inhalers on the other hand, can contain a much higher number of doses, whereas the number of handlings to prime a dose is generally lower.

Because the inspiratory air stream in multi-dose devices is often straight across the dose measuring cavity, and because the massive and rigid dose measuring systems of multi dose inhalers can not be agitated by this inspiratory air stream, the powder mass is simply entrained from the cavity and little de-agglomeration is obtained during discharge.

Consequently, separate disintegration means are necessary. However in practice, they are not always part of the inhaler design. Because of the high number of doses in multi-dose devices, powder adhesion onto the inner walls of the air conduits and the de-agglomeration means must be minimized and/or regular cleaning of these parts must be possible, without affecting the residual doses in the device. Some multi dose inhalers have disposable drug containers that can be replaced after the prescribed number of doses has been taken (e. g. WO 97/000703). For such semi-permanent multi dose inhalers with disposable drug containers, the requirements to prevent drug accumulation are even stricter.

In a preferred embodiment, the aclidinium is administered via a breath-activated, multidose, dry powder inhaler, calibrated to permit daily dosing of 400 µg metered nominal dose of aclidinium. An especially preferred inhaler device for this purpose is Genuair®, (formerly known as Novolizer SD2FL), or as described in WO 97/000703, WO 03/000325, or WO 03/061742, the contents of which applications are incorporated herein by reference.

Apart from applications through dry powder inhalers the compositions of the invention can be administered in aerosols which operate via propellant gases or by means of so-called atomisers or nebulizers, via which solutions or suspensions of pharmacologically-active substances can be sprayed under high pressure so that a mist of inhalable particles results.

Medicaments for administration by inhalation desirably have a controlled particle size. The optimum particle size for inhalation into the bronchial system is usually 1-10 µm, preferably 2-5 µm. Particles having a size above 20µ are generally too large when inhaled to reach the small airways. To achieve these particle sizes the particles of the active ingredient as produced may be size reduced by conventional means eg by micronisation or supercritical fluid techniques. The desired fraction may be separated out by air classification or sieving. Preferably, the particles will be crystalline.

Achieving a high dose reproducibility with micronised powders is difficult because of their poor flowability and extreme agglomeration tendency. To improve the efficiency of dry powder compositions, the particles should be large while in the inhaler, but small when discharged into the respiratory tract. Thus, an excipient, for example a mono-, di- or polysaccharide or sugar alcohol, e.g., such as lactose, mannitol or glucose is generally employed. The particle size of the excipient will usually be much greater than the inhaled medicament within the present invention. When the excipient is lactose it will typically be present as lactose particles, preferably crystalline alpha lactose monohydrate, e.g., having an average particle size range of 20-1000 µm, preferably in the range of 90-150 µm. The median particle size approximately corresponds to the average and is the diameter where 50 mass-% of the particles have a larger equivalent diameter, and the other 50 mass-% have a smaller equivalent diameter. Hence the average particle size is generally referred to in the art as equivalent d50. The distribution of particle size around may affect flow properties, bulk density, etc. Hence to characterize a particle size diameter, other equivalent diameters can be used in addition to d50, such as d10 and d90. d10 is the equivalent diameter where 10 mass-% of the particles have a smaller diameter (and hence the remaining 90% is coarser). d90 is the equivalent diameter where 90 mass-% of the particles have a smaller diameter. In one embodiment, the lactose particles for use in formulations of the invention have a d10 of 90-160 µm, a d50 of 170-270 µm, and d90 of 290-400 µm.

Suitable lactose materials for use in the present invention are commercially available, e.g., from DMW Internacional (Respitose GR-001, Respitose SV-001, Respitose SV-003); Meggle (Capsulac 60, Inhalac 70, Capsulac 60 INH); and Borculo Domo (Lactohale 100-200, Lactohale 200-300, and Lactohale 100-300).

The ratio between the lactose particles and the aclidinium by weight will depend on the inhaler device used, but is typically, e.g., 5:1 to 100:1, for example 25:1 to 75:1, e.g., 30-35:1.

In a preferred embodiment, the aclidinium is administered in the form of a dry powder formulation of aclidinium bromide in admixture with lactose, in a ratio by weight of aclidinium to lactose of 1:50 to 1:75, suitable for administration via a dry powder inhaler, wherein the aclidinium particles have an average particle size of from 2 to 5 µm in diameter, e.g., less than 3 µm in diameter, and the lactose particles have have a d10 of 90-160 µm, a d50 of 170-270 µm, and d90 of 290-400 µm.

Additional active agents such as β2-agonists, PDE IV inhibitors, corticosteroids, leukotriene D4 antagonists, inhibitors of egfr-kinase, p38 kinase inhibitors or NK1 receptor agonists may be utilized in the methods and formulations of the inventions. For example, the invention provides aclidinium formulations as described herein further comprising an effective amount of one or more such additional active agents, e.g. further comprising an effective amount of a β2-agonist and/or a PDE IV inhibitor and/or a corticosteroid. The invention also provides methods for treating respiratory conditions as herein before described, e.g., asthma or COPD, comprising administering an aclidinium formulation as described herein and further comprising administering simultaneously an effective amount of one or more such additional active agents, e.g. further comprising an effective amount of a β2-agonist and/or a PDE IV inhibitor and/or a corticosteroid.

β2-agonists suitable for use with the aclidinium in the present invention include, e.g., arformoterol, bambuterol, bitolterol, broxaterol, carbuterol, clenbuterol, dopexamine, fenoterol, formoterol, hexoprenaline, ibuterol, isoetharine, isoprenaline, levosalbutamol, mabuterol, meluadrine, metaproterenol, nolomirole, orciprenaline, pirbuterol, procaterol, reproterol, ritodrine, rimoterol, salbutamol, salmefamol, salmeterol, sibenadet, sotenerot, sulfonterol, terbutaline, tiaramide, tulobuterol, GSK-597901, milveterol, GSK-678007, GSK-642444, GSK-159802, HOKU-81, LAS 100977 (5-(2-{[6-(2,2-difluoro-2-phenylethoxy)hexyl]amino}-1(R)-hydroxyethyl)-8-hydroxyquinolin-2(1H)-one), KUL-1248, carmoterol, indacaterol and 5-[2-(5,6-diethylindan-2-ylamino)-1-hydroxyethyl]-8-hydroxy-1H-quinolin-2-one, 4-hydroxy-7-[2-{[2-{[3-(2-phenylethoxy)propyl]sulfonyl} ethyl]amino}ethyl]-2(3H)-benzothiazolone, 1-(2-fluoro-4-hydroxyphenyl)-2-[4-(1-benzimidazolyl)-2-methyl-2-butylamino]ethanol, 1-[3-(4-methoxybenzylamino)-4-hydroxyphenyl]-2-[4-(1-benzimidazolyl)-2-methyl-2-butylamino]ethanol, 1-[2H-5-hydroxy-3-oxo-4H-1,4-benzoxazin-8-yl]-2-[3-(4-N,N-dimethylaminophenyl)-2-methyl-2-propylamino]ethanol, 1-[2H-5-hydroxy-3-oxo-4H-1,4-benzoxazin-8-yl]-2-[3-(4-methoxyphenyl)-2-methyl-2-propylamino]ethanol, 1-[2H-5-hydroxy-3-oxo-4H-1,4-benzoxazin-8-yl]-2-[3-(4-n-butyloxyphenyl)-2-methyl-2-propylamino]ethanol, 1-[2H-5-hydroxy-3-oxo-4H-1,4-benzoxazin-8-yl]-2-{4-[3-(4-methoxyphenyl)-1,2,4-triazol-3-yl]-2-methyl-2-butylamino}ethanol, 5-hydroxy-8-(1-hydroxy-2-isopropylaminobutyl)-2H-1,4-benzoxazin-3-(4H)-one, 1-(4-amino-3-chloro-5-trifluoromethylphenyl)-2-tert-butylamino)ethanol and 1-(4-ethoxycarbonylamino-3-cyano-5-fluorophenyl)-2-(tert-butylamino)ethanol optionally in the form of their racemates, their enantiomers, their diastereomers, and mixtures thereof, and optionally their pharmacologically-compatible acid addition salts.

The preferred (β2-agonists to be used in the combinations of the invention are: arformoterol, bambuterol, bitolterol, broxaterol, carbuterol, clenbuterol, dopexamine, fenoterol, formoterol, hexoprenaline, ibuterol, isoprenaline, levosalbutamol, mabuterol, meluadrine, nolomirole, orciprenaline, pirbuterol, procaterol, (R,R)-formoterol, reproterol, ritodrine, rimoterol, salbutamol, salmeterol, sibenadet, sulfonterol, terbutaline, tulobuterol, GSK-597901, milveterol, LAS 100977 (5-(2-{[6-(2,2-difluoro-2-phenylethoxy)hexyl] amino}-1(R)-hydroxyethyl)-8-hydroxyquinolin-2(1H)-one), KUL-1248, carmoterol and indacaterol optionally in the form of their racemates, their enantiomers, their diastereomers, and mixtures thereof, and optionally their pharmacologically-compatible acid addition salts.

Since the M3 antagonists of the invention have a long duration of action, it is preferred that they are combined with long-acting β2-agonists (also known as LABAs). The combined drugs could thus be administered once or twice a day.

Particularly preferred LABAs are formoterol, salmeterol and GSK-597901, milveterol, LAS 100977 (5-(2-{[6-(2,2-difluoro-2-phenylethoxy)hexyl]amino}-1(R)-hydroxyethyl)-8-hydroxyquinolin-2(1H)-one), KUL-1248, carmoterol and indacaterol optionally in the form of their racemates, their enantiomers, their diastereomers and mixtures thereof, and optionally their pharmacologically-compatible acid addition salts. More preferred are salmeterol, formoterol, LAS 100977 (5-(2-{[6-(2,2-difluoro-2-phenylethoxy)hexyl]amino}-1(R)-hydroxyethyl)-8-hydroxyquinolin-2(1H)-one), and indacaterol. Still more preferred are salmeterol, formoterol and LAS 100977 (5-(2-{[6-(2,2-difluoro-2-phenylethoxy)hexyl]amino}-1(R)-hydroxyethyl)-8-hydroxyquinolin-2(1H)-one), in particular salmeterol xinafoate, formoterol fumarate and LAS 100977 (5-(2-{[6-(2,2-difluoro-2-phenylethoxy)hexyl]amino}-1(R)-hydroxyethyl)-8-hydroxyquinolin-2(1H)-one).

For example, the invention provides a pharmaceutical composition for inhalation comprising aclidinium in the form of a dry powder of a pharmaceutically acceptable salt, e.g., bromide, in admixture with a pharmaceutically acceptable carrier, e.g., lactose particles, together with formoterol fumarate, (i) comprising a single metered nominal dose of aclidinium equivalent to about 400 µg aclidinium bromide together with a single metered nominal dose of about 5-25 µg (e.g. 6, 8.5, 12, 18 or 24 µg, for example 12 µg) formoterol fumarate or (ii) in a multidose dry powder inhaler device calibrated to provide a metered nominal dose of aclidinium equivalent to about 400 µg aclidinium bromide together with a meterd nominal dose of about 5-25 µg (e.g. 6, 8.5, 12, 18 or 24 µg, for example 12 µg) formotrol fumarate.

The pharmaceutical composition for inhalation comprising aclidinium and a β2-agonist, for example, formoterol or LAS 100977 (5-(2-{[6-(2,2-difluoro-2-phenylethoxy)hexyl]amino}-1(R)-hydroxyethyl)-8-hydroxyquinolin-2(1H)-one), can be administered one or more times per day. Preferably once or twice a day.

Examples of suitable PDE4 inhibitors that can be combined with aclidinium in the present invention are benafentrine dimaleate, etazolate, denbufylline, rolipram, cipamfylline, zardaverine, arofylline, filaminast, tipelukast, tofimilast, piclamilast, tolafentrine, mesopram, drotaverine hydrochloride, lirimilast, roflumilast, cilomilast, oglemilast, apremilast, 6-[2-(3,4-Diethoxyphenyl)thiazol-4-yl]pyridine-2-carboxylic acid (tetomilast), (R)-(+)-4-[2-(3-Cyclopentyloxy-4-methoxyphenyl)-2-phenylethyl]pyridine (CDP-840), N-(3,5-Dichloro-4-pyridinyl)-2-[1-(4-fluorobenzyl)-5-hydroxy-1H-indol-3-yl]-2-oxoacetamide (GSK-842470), 9-(2-

Fluorobenzyl)-N6-methyl-2-(trifluoromethyl)adenine (NCS-613), N-(3,5-Dichloro-4-pyridinyl)-8-methoxyquinoline-5-carboxamide (D-4418), N-[9-Methyl-4-oxo-1-phenyl-3,4,6,7-tetrahydropyrrolo[3,2,1-jk][1,4]benzodiazepin-3(R)-yl]pyridine-4-carboxamide, 3-[3-(Cyclopentyloxy)-4-methoxybenzyl]-6-(ethylamino)-8-isopropyl-3H-purine hydrochloride (V-11294A), 6-[3-(N,N-Dimethylcarbamoyl)phenylsulfonyl]-4-(3-methoxyphenylamino)-8-methylquinoline-3-carboxamide hydrochloride (GSK-256066), 4-[6,7-Diethoxy-2,3-bis(hydroxymethyl)naphthalen-1-yl]-1-(2-methoxyethyl)pyridin-2(1H)-one (T-440), (−)-trans-2-[3'-[3-(N-Cyclopropylcarbamoyl)-4-oxo-1,4-dihydro-1,8-naphthyridin-1-yl]-3-fluorobiphenyl-4-yl] cyclopropanecarboxylic acid (MK-0873), CDC-801, UK-500001, BLX-914, 2-carbomethoxy-4-cyano-4-(3-cyclopropylmethoxy-4-difluoromethoxyphenyl)cyclohexan 1-one, cis [4-cyano-4-(3-cyclopropylmethoxy-4-difluoromethoxyphenyl)cyclohexan-1-ol, 5(S)-[3-(Cyclopentyloxy)-4-methoxyphenyl]-3(S)-(3-methylbenzyl)piperidin-2-one (IPL-455903), ONO-6126 (Eur Respir J 2003, 22(Suppl. 45): Abst 2557) and the compounds claimed in the PCT patent applications number WO03/097613, WO2004/058729, WO 2005/049581, WO 2005/123693 and WO 2005/123692.

Examples of suitable corticosteroids and glucocorticoids that can be combined with aclidinium in the present invention are prednisolone, methylprednisolone, dexamethasone, dexamethasone cipecilate, naflocort, deflazacort, halopredone acetate, budesonide, beclomethasone dipropionate, hydrocortisone, triamcinolone acetonide, fluocinolone acetonide, fluocinonide, clocortolone pivalate, methylprednisolone aceponate, dexamethasone palmitoate, tipredane, hydrocortisone aceponate, prednicarbate, alclometasone dipropionate, Butixocort propionate, RPR-106541, halometasone, methylprednisolone suleptanate, mometasone furoate, rimexolone, prednisolone farnesylate, ciclesonide, deprodone propionate, fluticasone propionate, fluticasone furoate, halobetasol propionate, loteprednol etabonate, betamethasone butyrate propionate, flunisolide, prednisone, dexamethasone sodium phosphate, triamcinolone, betamethasone 17-valerate, betamethasone, betamethasone dipropionate, 21-Chloro-11beta-hydroxy-17alpha-[2-(methylsulfanyl)acetoxy]-4-pregnene-3,20-dione, Desisobutyrylciclesonide, hydrocortisone acetate, hydrocortisone sodium succinate, NS-126, prednisolone sodium phosphate, hydrocortisone probutate, prednisolone sodium metasulfobenzoate and clobetasol propionate, especially budesonide or mometasone.

For example, the invention provides a pharmaceutical composition for inhalation comprising aclidinium in the form of a dry powder of a pharmaceutically acceptable salt, e.g., bromide, in admixture with a pharmaceutically acceptable carrier, e.g., lactose particles, together with mometasone furoate, (i) comprising a single metered nominal dose of aclidinium equivalent to about 400 µg aclidinium bromide together with a single metered nominal dose of about 100-900 µg (e.g., 100, 110, 200, 220, 300, 330, 400, 440, 800 or 880 µg, for example 200-450, e.g 220 or 440 µg) mometasone furoate, or (ii) in a multidose dry powder inhaler device calibrated to provide a metered nominal dose of aclidinium equivalent to about 400 µg aclidinium bromide together with a metered nominal dose of about 100-900 µg (e.g. 100, 110, 200, 220, 300, 330, 400, 440, 800 or 880 µg, for example 200-450, e.g 220 or 440 µg) mometasone furoate.

The pharmaceutical composition for inhalation comprising aclidinium and a corticosteroid, for example mometasone furoate, can be administered one or more times per a day. Preferably once or twice a day.

The invention also provides a pharmaceutical composition comprising aclidinium, a β2-agonist as defined above and a corticosteroid, as defined above. Most preferred β2-agonists are selected from LAS 100977 ((5-(2-{[6-(2,2-difluoro-2-phenylethoxy)hexyl]amino}-1(R)-hydroxyethyl)-8-hydroxyquinolin-2(1H)-one) and formoterol. Most preferred corticosteroid is a mometasone furoate. These triple combinations are suitable for administration once or twice a day.

Example 1

Methods: Patients with moderate to severe stable COPD were randomized to receive double-blind, once-daily treatment with aclidinium (25, 50, 100, 200, or 400 µg), placebo, or open-label tiotropium 18 µg for 4 weeks. Spirometric measurements were performed at 22-24 h after the first dose and then at weekly intervals, and from 0.5-6 h post-administration on Day 1 and at Week 4 (Day 29).

Results: The ITT population included 460 patients. Aclidinium dose-dependently increased trough $FEV_1$ on Day 29 (table).

| Mean change from baseline in trough $FEV_1$ on Day 29 | | | | | | |
|---|---|---|---|---|---|---|
| | Aclidinium (double-blind) | | | | | Tiotropium (open-label) |
| | 25 µg | 50 µg | 100 µg | 200 µg | 400 µg | 18 µg |
| n | 65 | 65 | 69 | 66 | 67 | 64 |
| Mean Δ, ml | 39 | 36 | 83 | 148* | 128* | 161* |

*$p < 0.05$ vs placebo

Unlike tiotropium, the bronchodilatory effect of aclidinium during the first 6 h post-dose on Day 29 was comparable to that on Day 1 (all doses). Time to peak $FEV_1$ was achieved at 3 h post-dose for aclidinium 100-400 µg. Aclidinium was well tolerated, with no dose-dependent effect on ECG, laboratory parameters or adverse events.

Conclusion: Aclidinium produced sustained bronchodilation over 24 h and was well tolerated. Aclidinium 200 and 400 µg had comparable bronchodilatory effects to open-label tiotropium 18 µg. Based on the efficacy and tolerability data, aclidinium 400 µg is selected as the investigational dose for a future long-term clinical trial in COPD.

The invention claimed is:

1. A pharmaceutical composition comprising aclidinium bromide in admixture with a pharmaceutically acceptable dry powder carrier, wherein the pharmaceutical composition is in a dosage form which provides a) a metered nominal dose of 400 micrograms plus/minus 10% aclidinium bromide and b) an emitted dose of 360 micrograms plus/minus 35% aclidinium bromide, wherein the pharmaceutical composition is for inhalation.

2. The pharmaceutical composition according to claim 1, in the form of a single-dose dry powder formulation comprising a) a single metered nominal dose of 400 micrograms plus/minus 10% aclidinium bromide and b) a single emitted dose of 360 micrograms plus/minus 35% aclidinium bromide.

3. The pharmaceutical composition according to claim 1, in the form of a multi-dose dry powder formulation for administration in a multidose dry powder inhaler device calibrated to provide a metered nominal dose of 400 micrograms plus/minus 10% aclidinium bromide and b) an emitted dose of 360 micrograms plus/minus 35% aclidinium bromide.

4. The pharmaceutical composition according to claim 1, wherein the emitted dose is 360 micrograms plus/minus 10% aclidinium bromide.

5. The pharmaceutical composition according to claim 1, wherein the dosage form provides a fine particle dose of 120 micrograms plus/minus 35% aclidinium bromide.

6. The pharmaceutical composition according to claim 1, wherein the pharmaceutically acceptable carrier is lactose particles.

7. The pharmaceutical composition according to claim 1, wherein the ratio of aclidinium to carrier ranges from 1:25 to 1:75 by weight.

8. The pharmaceutical composition according to claim 7, wherein the ratio of aclidinium to carrier ranges from 1:50 to 1:75 by weight.

9. The pharmaceutical composition according to claim 7, wherein the average particle diameter of aclidinium bromide ranges from 2 μm to 5 μm.

10. The pharmaceutical composition according to claim 1, wherein the carrier comprises particles having a d10 ranging from 90 μm to 160 μm, a d50 ranging from 170 μm to 270 μm, and a d90 ranging from 290 μm to 400 μm.

11. The pharmaceutical composition according to claim 1, further comprising an effective amount of a β2-agonist.

12. The pharmaceutical composition according to claim 1, wherein the β2-agonist is formoterol or a pharmaceutically acceptable salt thereof.

13. The pharmaceutical composition according to claim 12, wherein the formoterol is formoterol fumarate in an amount ranging from about 5 micrograms to 25 micrograms per metered nominal dose.

14. The pharmaceutical composition according to claim 13, wherein the formoterol fumarate is present in an amount of about 12 micrograms per metered nominal dose.

15. A method of treating a respiratory condition chosen from asthma and chronic obstructive pulmonary disease, comprising administering a pharmaceutical composition comprising aclidinium bromide in admixture with a pharmaceutically acceptable dry powder carrier, wherein the pharmaceutical composition is in a dosage form which provides a) a metered nominal dose of 400 micrograms plus/minus 10% aclidinium bromide and b) an emitted dose of 360 micrograms plus/minus 35% aclidinium bromide, by inhalation to a patient in need of such treatment.

16. The method of claim 15, wherein the emitted dose is 360 micrograms plus/minus 10% aclidinium bromide.

17. The method of claim 15, wherein the dosage form provides a fine particle dose of 120 micrograms plus/minus 35% aclidinium bromide.

18. The method of claim 15, further comprising administering an effective amount of a β2-agonist.

19. The method of claim 18, wherein the β2-agonist is formoterol or a pharmaceutically acceptable salt thereof.

20. The method according to claim 18, wherein the β2-agonist is formoterol fumarate in an amount ranging from about 5 micrograms to 25 micrograms per metered nominal dose.

21. The method according to claim 20, wherein the formoterol fumarate is present in an amount of about 12 micrograms per metered nominal dose.

22. The method according to claim 15, wherein the pharmaceutical composition is administered twice-daily.

23. A multidose dry powder inhaler device comprising a pharmaceutical composition comprising aclidinium bromide in admixture with a pharmaceutically acceptable dry powder carrier, wherein the pharmaceutical composition is in a dosage form which provides a) a metered nominal dose of 400 micrograms plus/minus 10% aclidinium bromide and b) an emitted dose of 360 micrograms plus/minus 35% aclidinium bromide.

24. The multidose dry powder inhaler device according to claim 23, wherein the emitted dose is 360 micrograms plus/minus 10% aclidinium bromide.

25. The multidose dry powder inhaler device according to claim 23, wherein the dosage form provides a fine particle dose of 120 micrograms plus/minus 35% aclidinium bromide.

26. The multidose dry powder inhaler device according to claim 23, wherein the pharmaceutical composition further comprises a β2-agonist.

27. The multidose dry powder inhaler device according to claim 26, wherein the β2-agonist is formoterol or a pharmaceutically acceptable salt thereof.

28. The multidose dry powder inhaler device according to claim 27, wherein the β2-agonist is formoterol fumarate in an amount ranging from about 5 micrograms to 25 micrograms per metered nominal dose.

29. The multidose dry powder inhaler device according to claim 28, wherein the formoterol fumarate is present in an amount of about 12 micrograms per metered nominal dose.

* * * * *